(12) United States Patent
Meltola et al.

(10) Patent No.: US 9,944,657 B2
(45) Date of Patent: *Apr. 17, 2018

(54) LUMINESCENT LANTHANIDE CHELATES HAVING THREE CHROMOPHORES AN THEIR USE

(75) Inventors: Niko Meltola, Piispanristi (FI); Harri Takalo, Turku (FI)

(73) Assignee: Radiometer Turku Oy, Turku (FI)

( * ) Notice: Subject to any disclaimer, the term of this patent is extended or adjusted under 35 U.S.C. 154(b) by 644 days.

This patent is subject to a terminal disclaimer.

(21) Appl. No.: 13/589,027

(22) Filed: Aug. 17, 2012

(65) Prior Publication Data

US 2013/0210165 A1    Aug. 15, 2013

Related U.S. Application Data

(60) Provisional application No. 61/578,977, filed on Dec. 22, 2011.

(30) Foreign Application Priority Data

Aug. 19, 2011 (DK) .................................. 2011 00630

(51) Int. Cl.
C07F 5/00 (2006.01)
G01N 21/64 (2006.01)
C07D 213/79 (2006.01)

(52) U.S. Cl.
CPC ............ C07F 5/003 (2013.01); C07D 213/79 (2013.01); G01N 21/6486 (2013.01)

(58) Field of Classification Search
None
See application file for complete search history.

(56) References Cited

U.S. PATENT DOCUMENTS

| | | | | |
|---|---|---|---|---|
| 7,018,851 | B2 * | 3/2006 | Takalo et al. .............. | 436/546 |
| 2002/0188111 | A1 | 12/2002 | Raymond et al. | |
| 2004/0166585 | A1 * | 8/2004 | Takalo et al. .............. | 436/172 |
| 2014/0017807 | A9 * | 1/2014 | Meltola et al. ............. | 436/501 |

FOREIGN PATENT DOCUMENTS

| | | |
|---|---|---|
| EP | 0 967 205 A1 | 12/1999 |
| EP | 1 447 666 A2 | 8/2004 |
| JP | H 1-502271 | 8/1989 |
| WO | WO 00/48990 | 8/2000 |
| WO | WO 00/48991 | 8/2000 |
| WO | WO 2006/026038 A1 | 3/2006 |
| WO | WO 2008/020113 A1 | 8/2008 |

OTHER PUBLICATIONS

Takalo et al., "Synthesis and Luminescence of Novel EuIII Complexing Agents and Labels with 4-(Phenylethynyl)pyridine Subunits," Helvetica Chimica Acta, 1996, vol. 79, pp. 789-802.*
Latva et al., "Correlation between the lowest triplet state energy level of the ligand and lanthanide(III) luminescence quantum yield," J. Luminescence, 1997, vol. 75, issue 2, pp. 149-169.*
Scorilas et al., "Streptavidin-polyvinylamine conjugates labeled with a europium chelate: applications in immunoassay, immunohistochemistry, and microarrays," Clin. Chem., 2000, vol. 46, No. 9, pp. 1450-1455.*
Hashino et al., "Application of a fluorescent lanthanide chelate label on a solid support device for detecting DNA variation with ligation-based assay," Anal. Biochem., 2007, vol. 364, issue 1, pp. 89-91; Epub Feb. 13, 2007.*
Cummins et al., "Application of europium(III) chelate-dyed nanoparticle labels in a competitive atrazine fluoroimmunoassay on an ITO waveguide," Biosens. Bioelectron., 2006, vol. 21, No. 7, pp. 1077-1085.*
International Search Report and Written Opinion dated Nov. 29, 2012.
Alcock N.W. et al., "Complexes of 2,6-bis[N-(2'-pyridlymethyl)carbamyl]pyridine; formation of mononuclear complexes, and self-assembly of double helical dinuclear and tetranuclear copper(II) complexes," Dalton Transactions, vol. 3, pp. 518-527 (2005).
Lode P. et al., "A Europlum Chelate for Quantitative Point-of-Care Immunoassays Using Direct Surface Measurement," Anal. Chem., vol. 75, No. 13, pp. 3193-3201 (2003).
Newkome G.R. et al., "Multidentate Ligands Containing 2,2'-Bipyridine and/or Pyridine Moieties: Structural Aspects of Their Octahedral and Pentagonal-Bipyramidal Complexes," Inorganic Chemistry, vol. 23, No. 16, pp. 2400-2408 (1984).
Petterson et al. "Multi-Assay Point-of-Care Platform: Highly Sensitive Time-Resolved Fluorometric Detection in Combination with a Universal 'All-In-One' Assay Format," *Point of Care*, 3: 225-232 (2003).

* cited by examiner

*Primary Examiner* — Galina Yakovleva
(74) *Attorney, Agent, or Firm* — Finnegan, Henderson, Farabow, Garrett & Dunner, LLP

(57) ABSTRACT

The present application discloses a luminescent lanthanide chelate of formula (I)

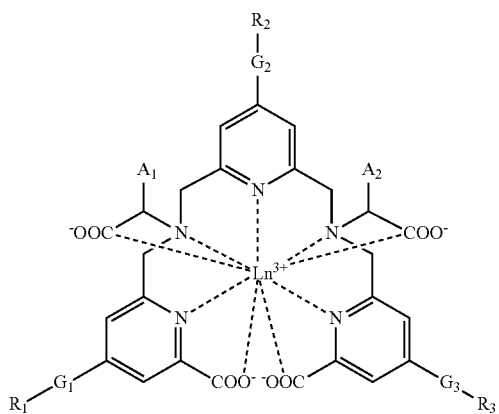

with lanthanides such as europium, as well as the corresponding luminescence lanthanide chelating ligand. The application also discloses a detectable molecule comprising a biospecific binding reactant (such as an antibody) conjugated to the luminescent lanthanide chelate as well as a method of carrying out a biospecific binding assay, the use of such a detectable molecule in a specific bioaffinity based assay, the use of such a detectable molecule in a specific bioaffinity based binding assay utilizing time-resolved fluorometric determination of a specific luminescence, and a solid support material conjugated with the luminescent lanthanide chelate.

13 Claims, 15 Drawing Sheets

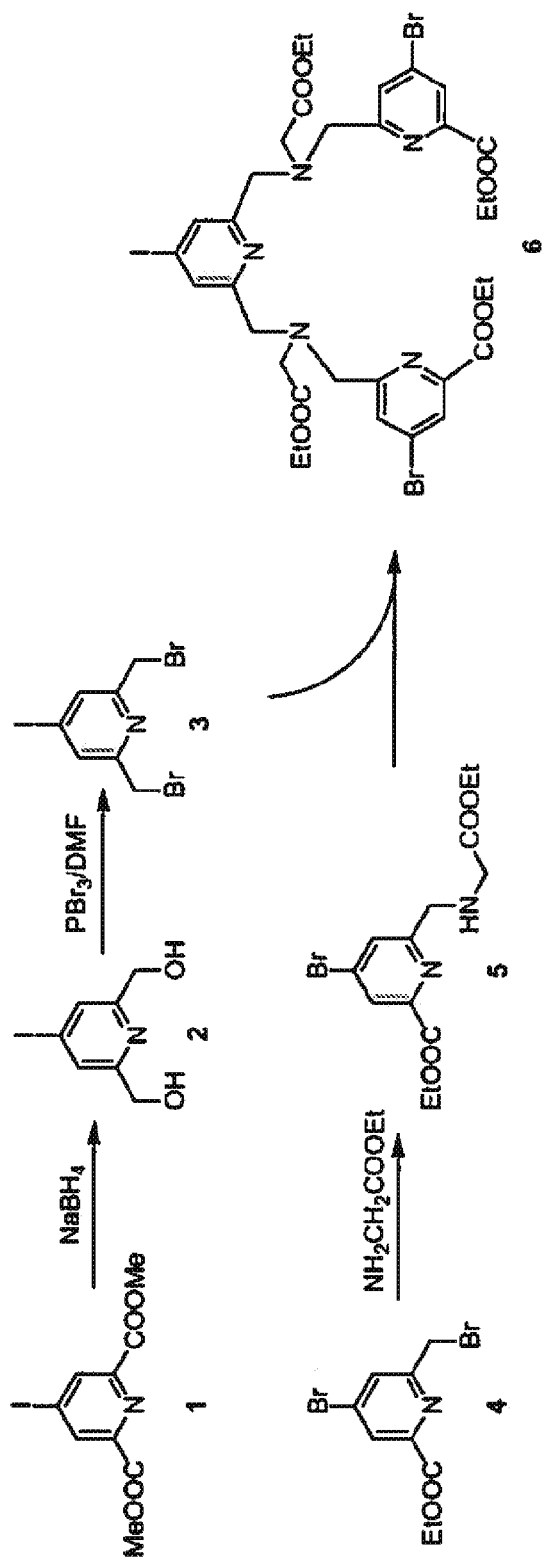
FIG. 1. Synthesis of compound 6.

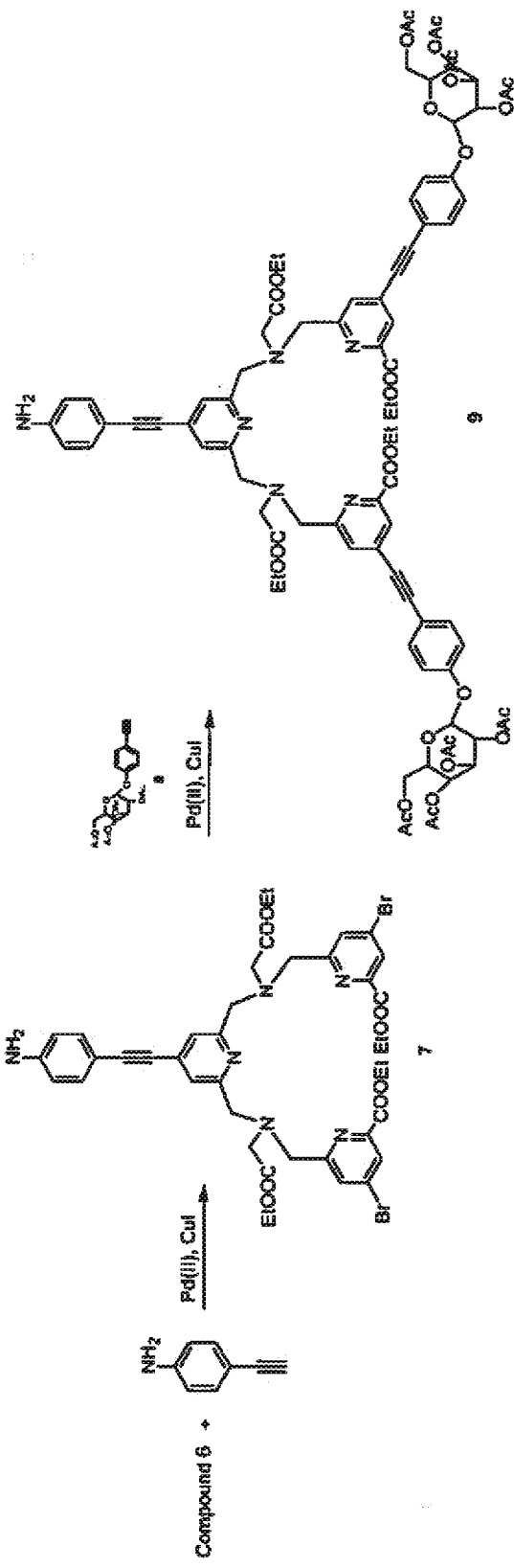
FIG. 2. Synthesis of compound 9.

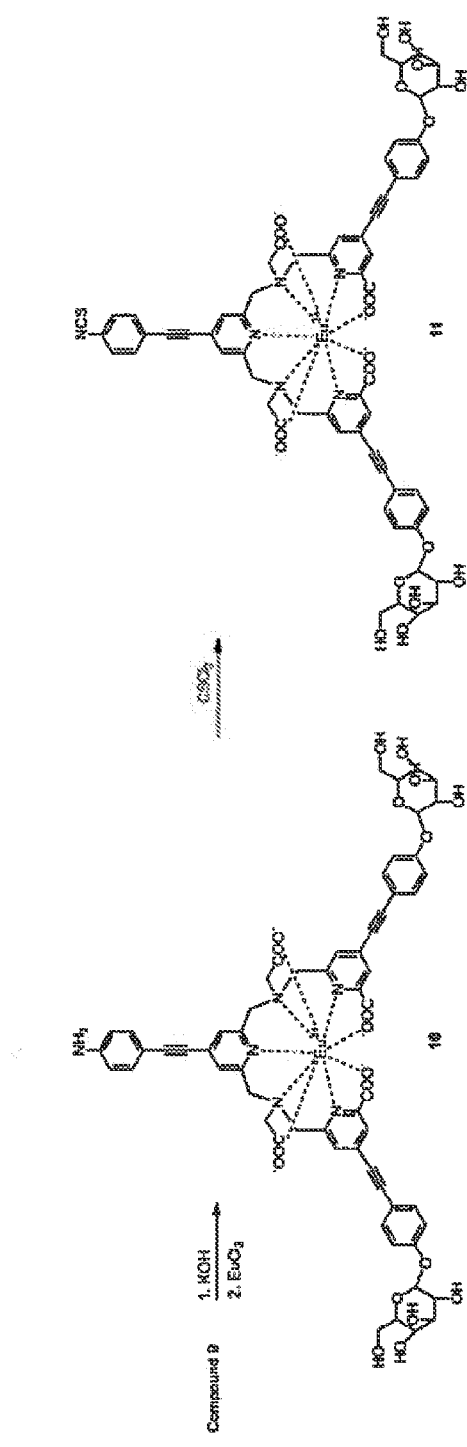
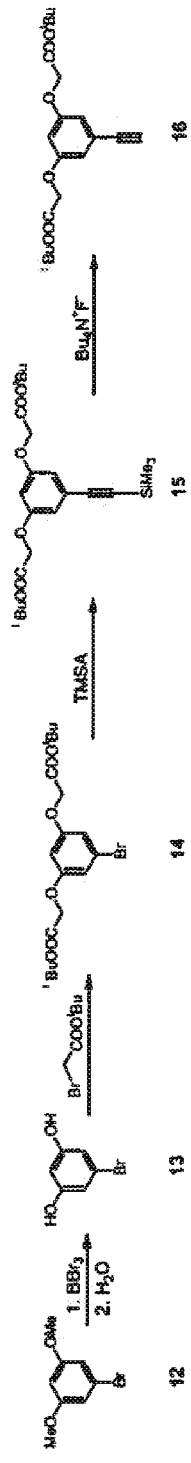
FIG. 3A. Synthesis of compound 11.
FIG. 3B. Synthesis of compound 16.

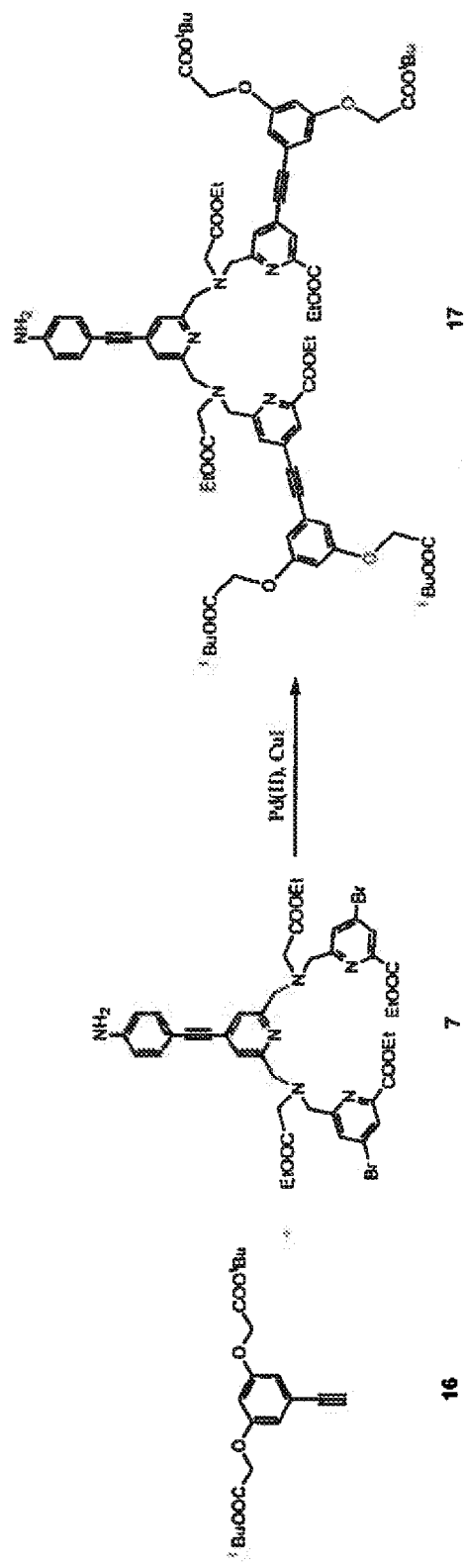
FIG. 4. Synthesis of compound 17.

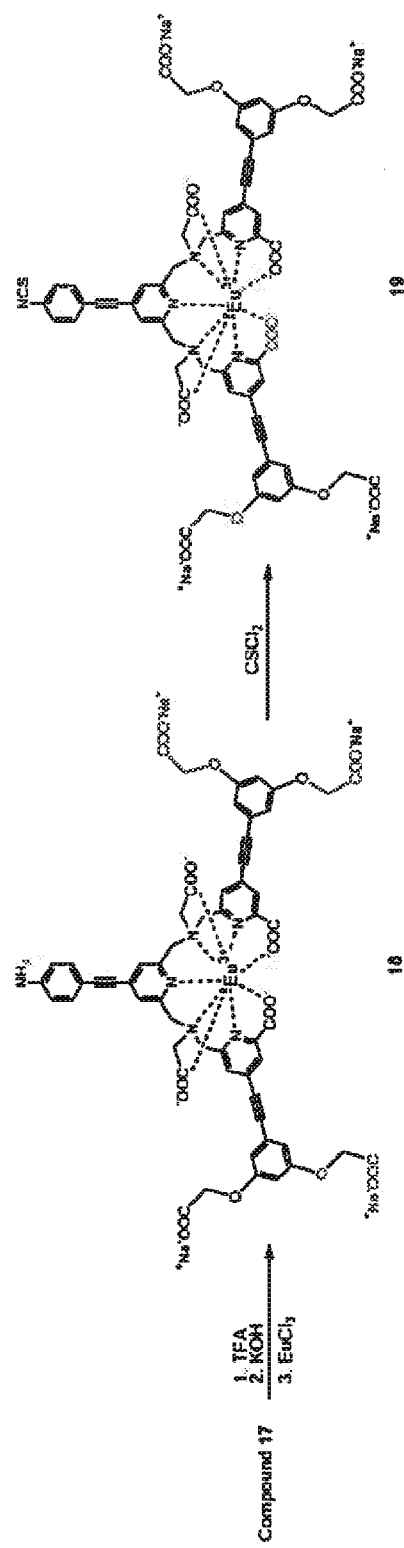
FIG. 5. Synthesis of compound 19.

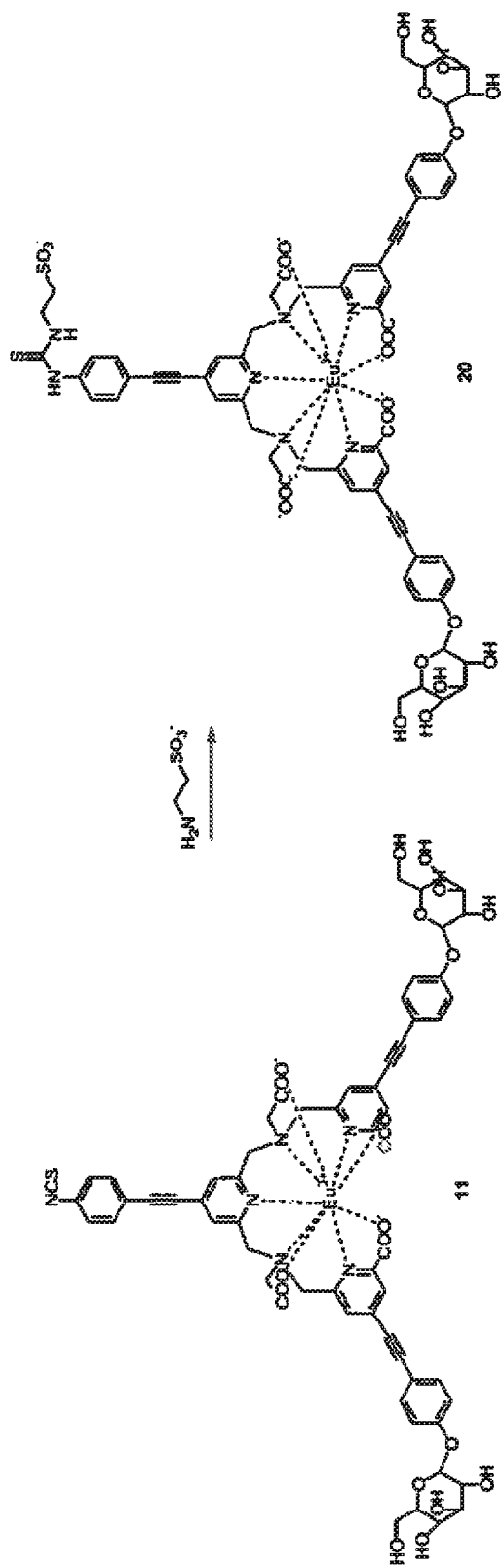
FIG. 6. Synthesis of compound 20.

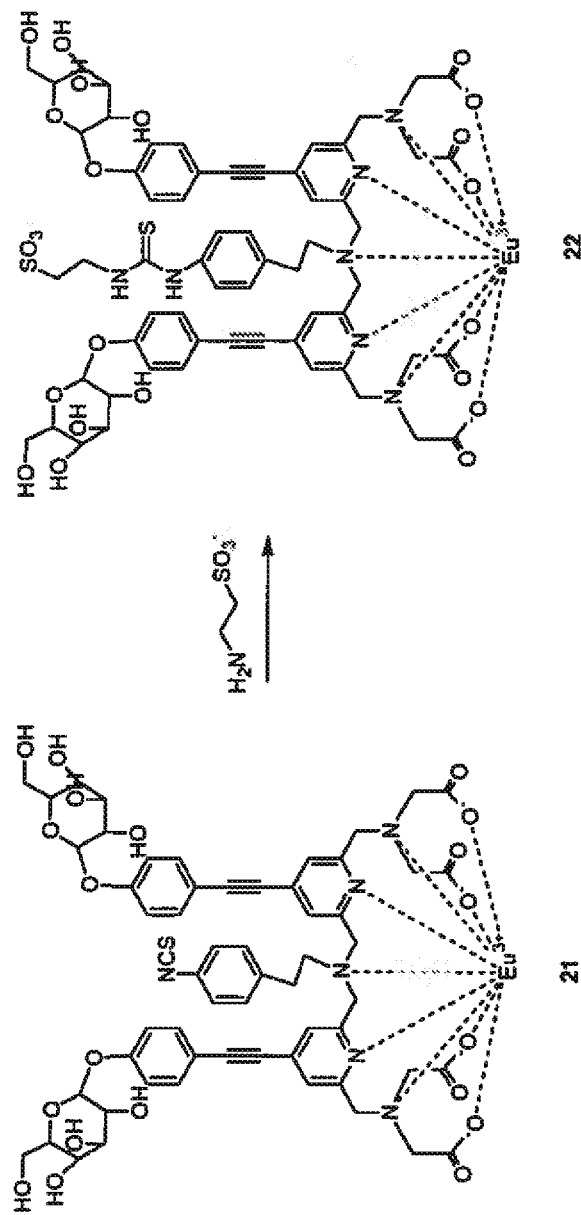
FIG. 7. Synthesis of compound 22.

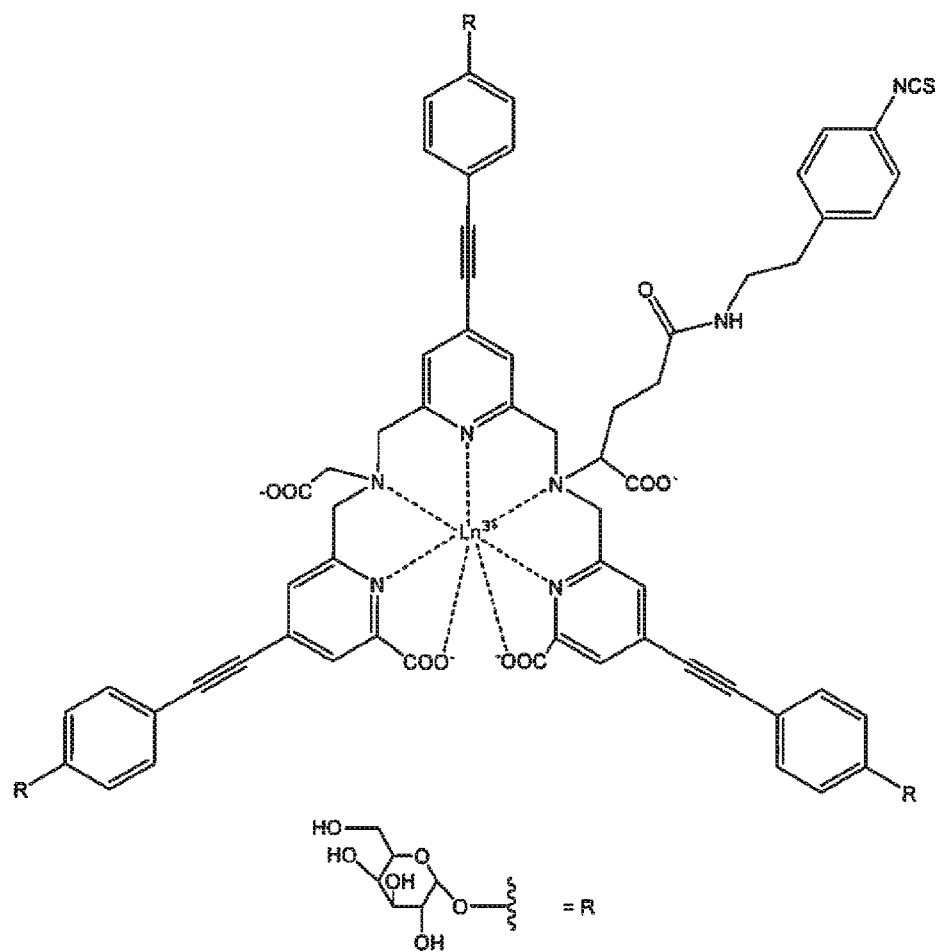
FIG. 8. Prospect Luminescent Lanthanide Chelate

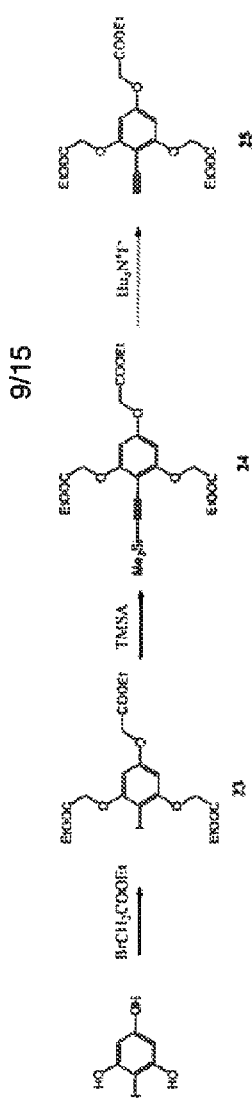
FIG. 9A. Synthesis of compound 25.
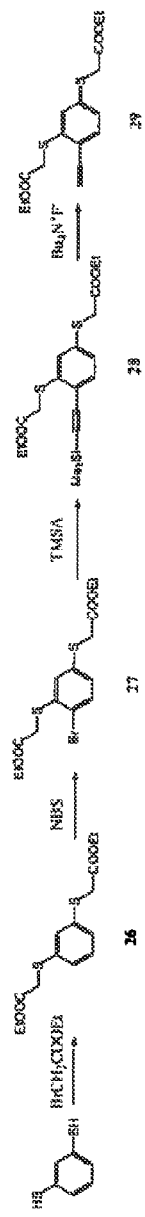
FIG. 9B. Synthesis of compound 29.
FIG. 9C. Synthesis of compound 32.

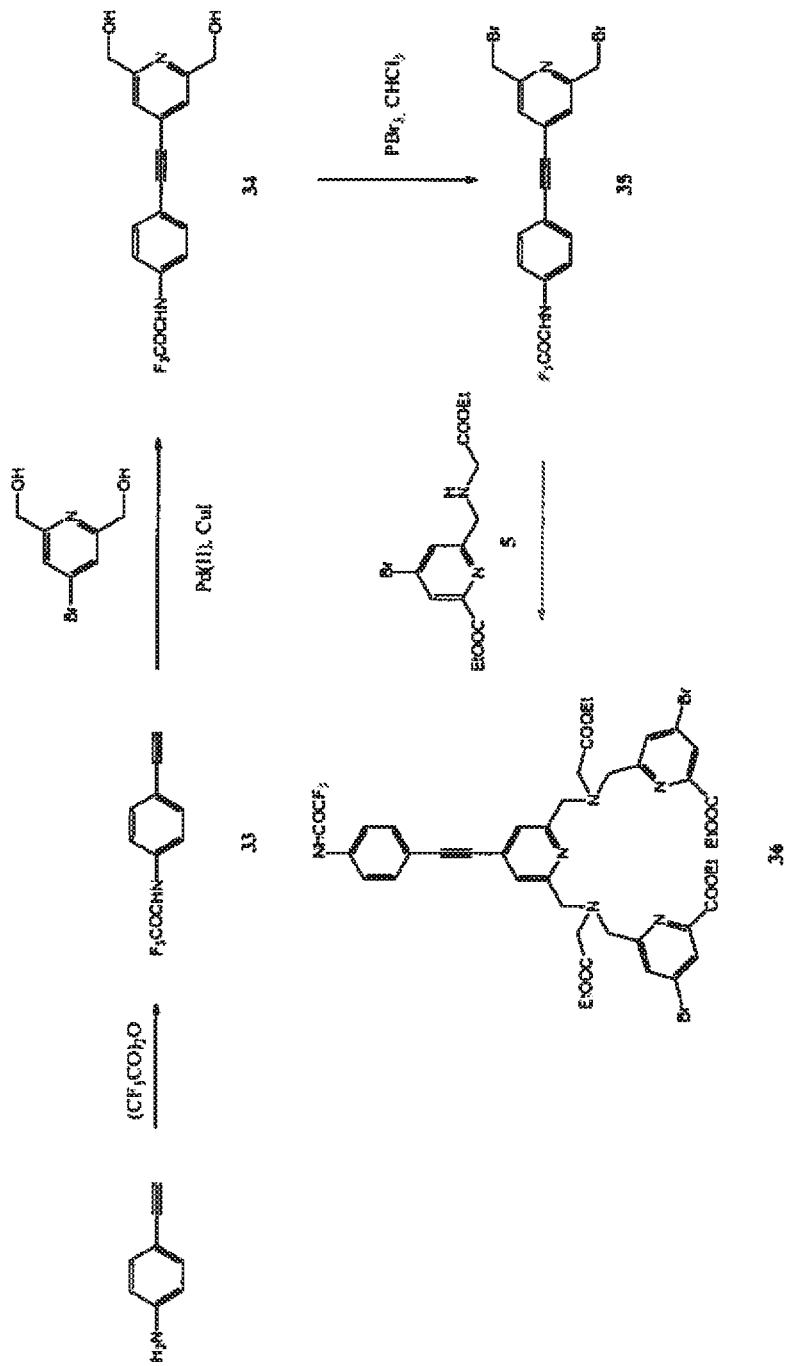
FIG. 10. Synthesis of compound 36.

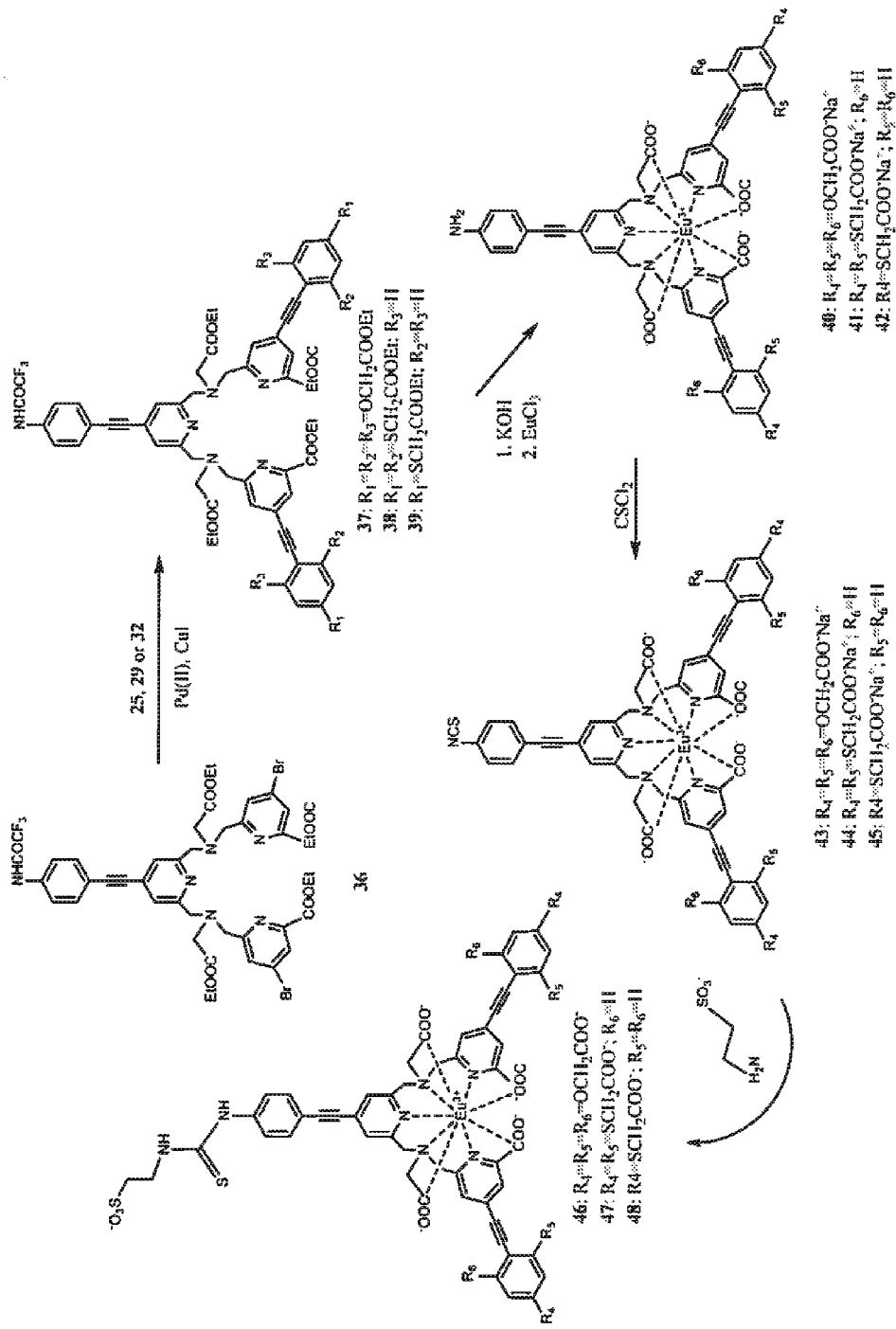
FIG. 11. Synthesis of labeling reagents 43-45 and their taurine derivatives 46-48.

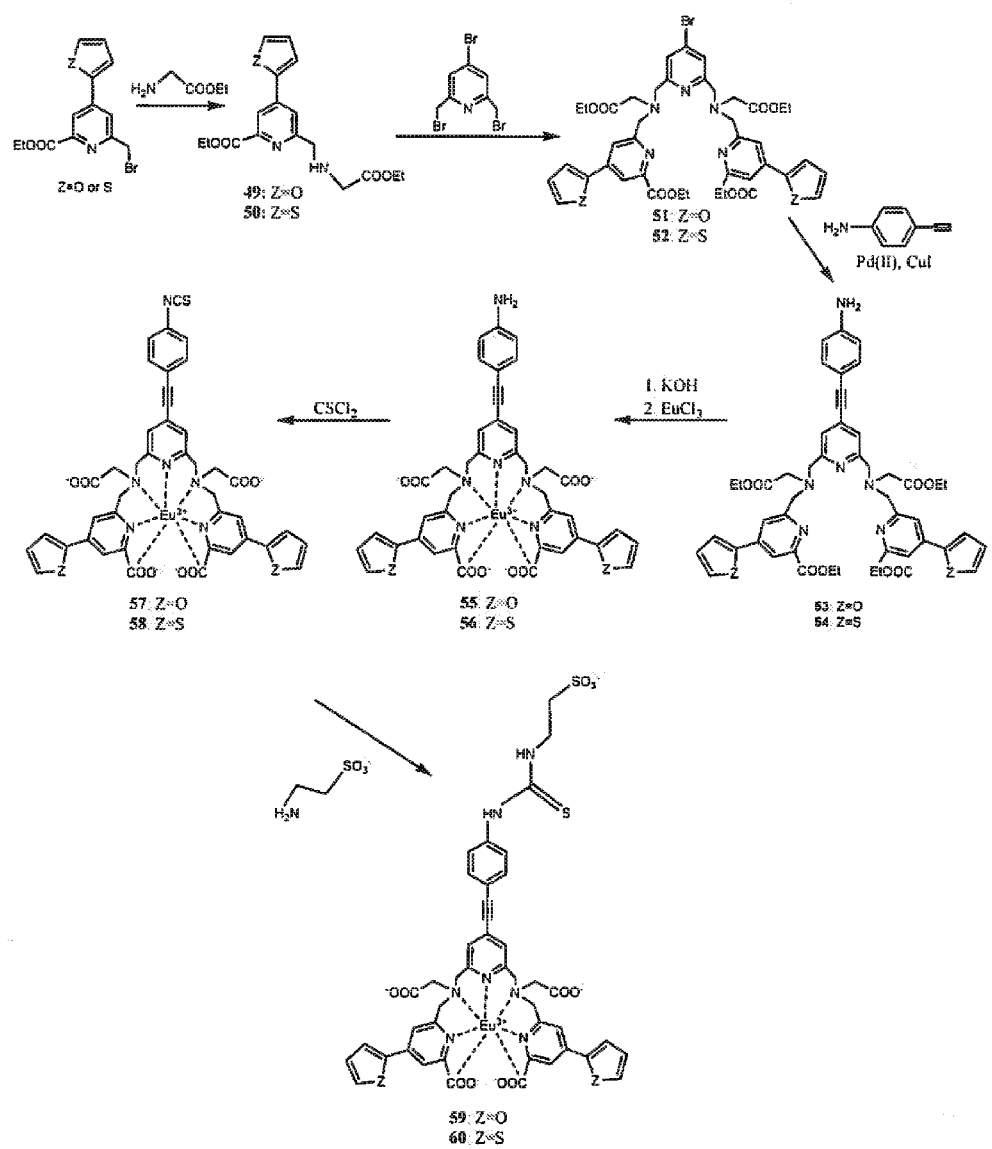
FIG. 12. Synthesis of compound 44.

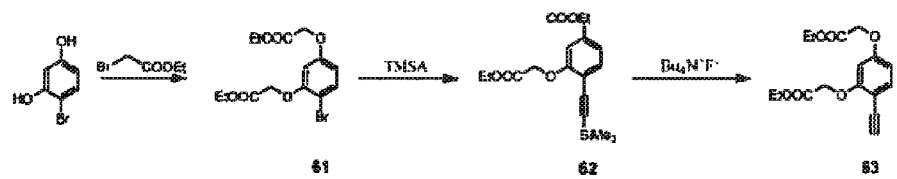
FIG. 13A. Synthesis of compound 63.
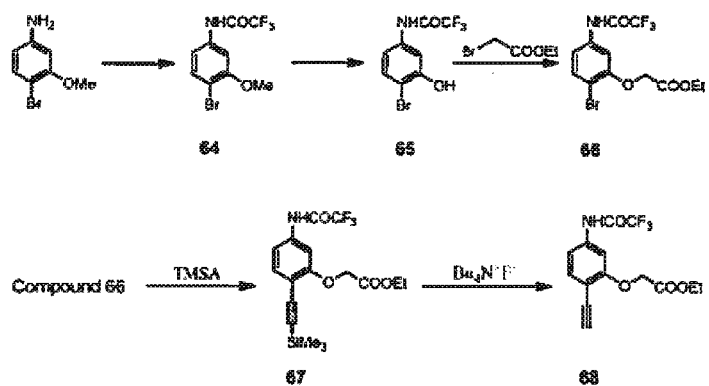
FIG. 13B. Synthesis of compound 68
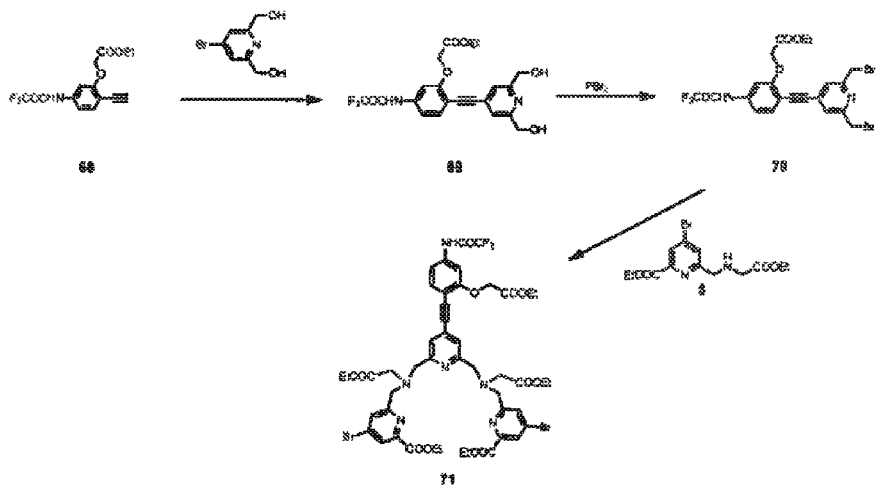
FIG. 13C. Synthesis of compound 71

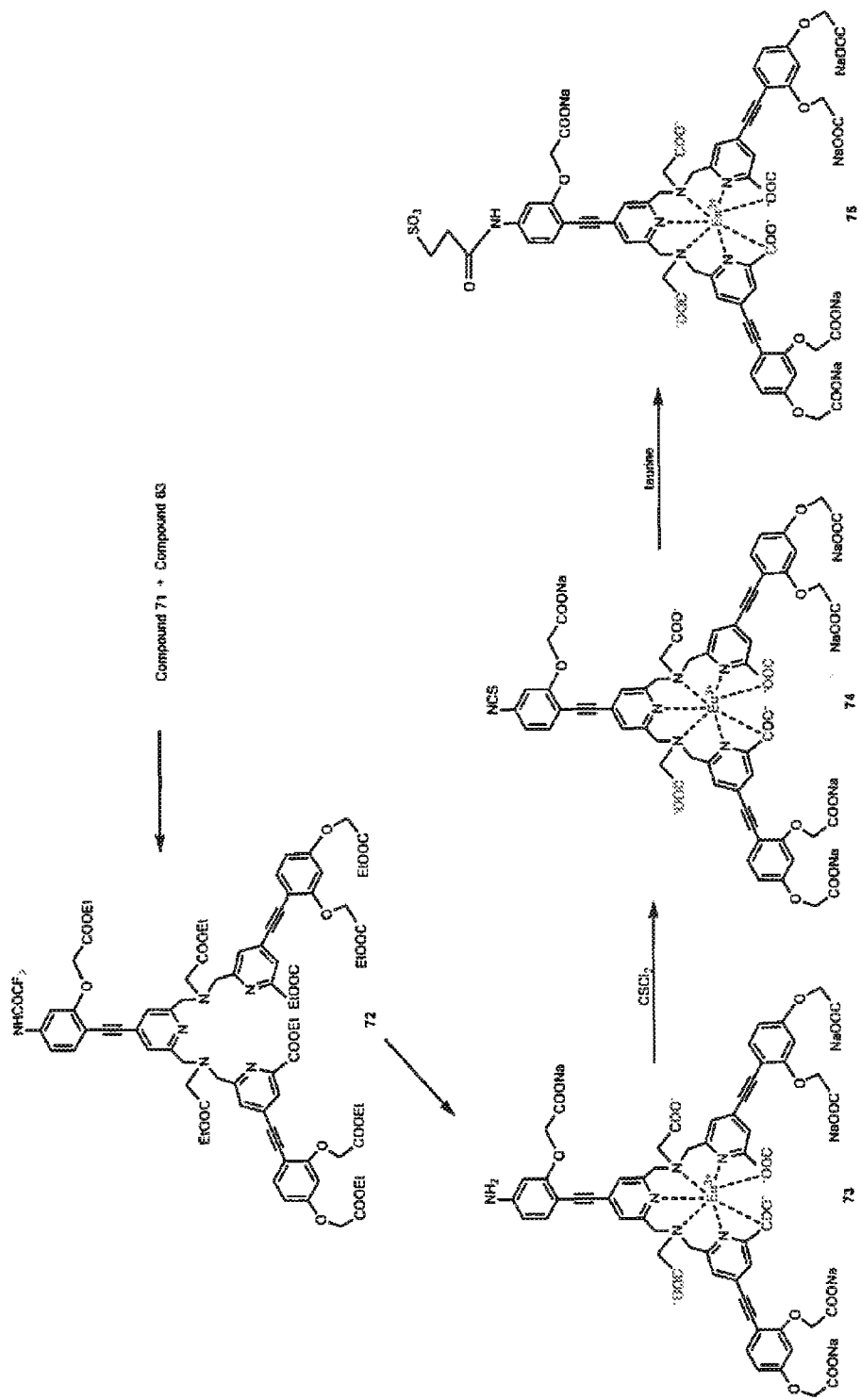
FIG. 14. Synthesis of labeling reagent 74 and its taurine derivative 75.

LUMINESCENT LANTHANIDE CHELATES HAVING THREE CHROMOPHORES AN THEIR USE

CROSS-REFERENCE TO RELATED APPLICATION

This application claims priority to U.S. Provisional Application No. 61/578,977, filed Dec. 22, 2011 and Danish Patent Application No. PA2011 00630, filed Aug. 19, 2011, each of which is hereby incorporated by reference in its entirety.

FIELD OF INVENTION

The present invention relates to novel three-chromophore-containing lanthanide chelates to be attached to a biospecific reactant and their use in various assays.

BACKGROUND OF INVENTION

Time-resolved fluorometry (TRF) employing long-lifetime emitting luminescent lanthanide chelates has been applied in many specific binding assays, such as e.g. immunoassays, DNA hybridization assays, receptor-binding assays, enzymatic assays, bio-imaging such as immunocytochemical, immunohistochemical assays or cell based assays to measure wanted analyte at very low concentration. Moreover, lanthanide chelates have been used in magnetic resonance imaging (MRI) and position emission tomography (PET)

For TRF application, an optimal label has to fulfill several requirements. First, it has to be photochemically stable both in the ground state and in the excited state and it has to be kinetically and chemically stable. The excitation wavelength has to be as high as possible, preferable over 300 nm. It has to have efficient cation emission i.e. high luminescence yield (excitation coefficient x quantum yield, $\epsilon\Phi$). The observed luminescence decay time has to be long, and the chelate has to have good water solubility. For the purpose of labeling, it should have a reactive group to allow covalent attachment to a biospecific binding reactant, and the affinity and nonspecific binding properties of the labeled biomolecules have to be retained.

The challenge is to prepare a chelate label to fulfill all requirements in one molecule, and therefore, certain compromises are generally made in the development of suitable labels. As a consequence hereof, a number of attempts (see e.g. the review in Bioconjugate Chem., 20 (2009) 404) have been made to tune the photo-physical properties of the chelate labels suitable for time-resolved fluorometric applications.

One generally used method to improve luminescence intensity is to prepare chelate ligands with several independent chromophoric moieties combined in structure designs, which offer high stabilities and luminescence quantum yields. Chelates which contain two and three separate 4-(phenylethynyl)pyridines are published by Takalo, H., et al., 1996, Helv. Chim. Acta., 79, 789. More recent examples of lanthanide chelates and chelating ligands are those disclosed in e.g. EP 1 447 666, WO 2010/055207, WO 2010/006605 and WO 2008/020113. Based on chelate stability studies with cyclic azamacrocycles (such as DOTA), higher stabilities over open chain chelates (such as DPTA) has been observed, and thus, the main focus with disclosed chelates with three chromophores has been on azamacrocycles tethered to the various chromophores.

Lately, high lanthanide chelate stabilities have been observed with open chain ligands utilizing several 1-hydroxy-2-pyridinone and salisylamide groups although these disclosed chelates are normally eight dentate and do not contain carboxylic acids for coordination to a lanthanide ion, high luminescence and stabilities have been obtained. However, those lanthanide chelates have only moderate total molar absorptivity i.e. below 27,000 with four chromophores, whereas e.g. chelates with only one phenylethynylpyridine subunit normally have absorptivities of 25,000-35,000 cm-[1] (Latva, M, et al., 1997, J. Luminescence, 75, 149) depending on the substituents in the chromophore.

A well-known challenge with chelates and ligands having many chromophores is to find out a suitable structure design, which offers high water solubility and at the same time being inert towards any possible bioprocesses. It is known, that the addition of chromophores decreases the solubility of ligands and chelates in water, increases the formation of biospecific binding reactant aggregates during the labeling process and non-specific binding properties of labeled biomolecules. Aggregates will produce purification problems and reduced yield of labeled material. Moreover, increased non-specific binding of labeled biomolecule will enhance back-ground luminescence of biospecific assays and thus reduces assay sensitivity.

SUMMARY OF INVENTION

The invention relates to a novel label chelate design having three individual chromophors around an emitting lanthanide ion and giving exceptionally high signal level.

With the chelates of the invention it is possible to decrease the labelling degree without losing signal, and at the same time the lower degree of labelling will improve the affinity of the biomolecule and decrease unspecific binding during the assay. Thus faster kinetic is possible and lower background is seen which can also improve the overall assay sensitivity.

A first aspect of the invention relates to a luminescent lanthanide chelate formula (I)

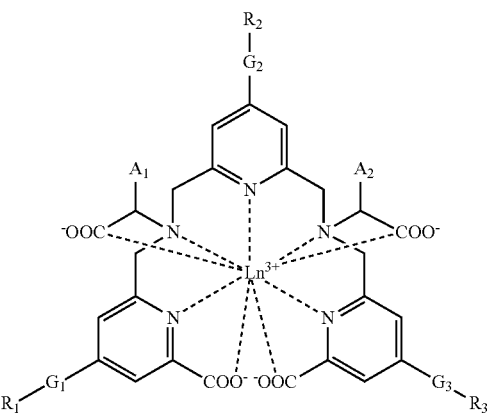

A second aspect of the invention relates to a detectable molecule comprising a biospecific binding reactant conjugated to a luminescent lanthanide chelate of the formula (I) as defined herein.

A third aspect of the invention relates to a luminescent lanthanide chelating ligand of formula (II)

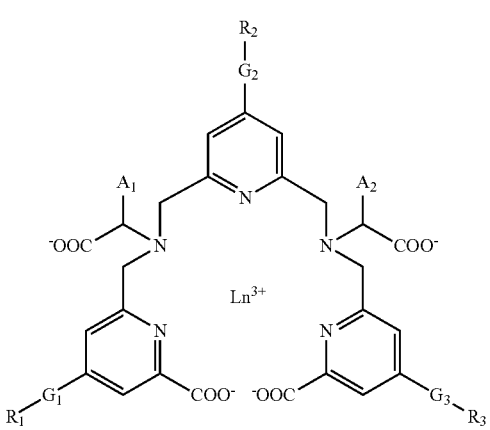

A fourth aspect of the invention relates to a method of carrying out a biospecific binding assay, said method comprising the steps of: a) forming a biocomplex between an analyte and a biospecific binding reactant labelled by the lanthanide chelate as defined herein,; b) exciting said biocomplex with radiation having an excitation wavelength, thereby forming an excited biocomplex; and c) detecting emission radiation emitted from said excited biocomplex.

A fifth aspect of the invention relates to the use of a detectable molecule as defined herein in a specific bioaffinity based binding assay utilizing time-resolved fluorometric determination of a specific luminescence.

A sixth aspect of the invention relates to a solid support material conjugated with a luminescent lanthanide chelate of the formula (I) as defined herein.

BRIEF DESCRIPTION OF THE FIGURES

FIG. 1 shows the synthesis of compound 6.
FIG. 2 shows the synthesis of compound 9.
FIG. 3A shows the synthesis of compound 11,
and FIG. 3B shows the synthesis of compound 16.
FIG. 4 shows the synthesis of compound 17.
FIG. 5 shows the synthesis of compound 19.
FIG. 6 shows the synthesis of compound 20.
FIG. 7 shows the synthesis of compound 22.
FIG. 8 shows a prospect luminescent lanthanide chelate.
FIG. 9A shows the synthesis of compound 25.
FIG. 9B shows the synthesis of compound 29,
and FIG. 9C shows the synthesis of compound 32.
FIG. 10 shows the synthesis of compound 36.
FIG. 11 shows the synthesis of labeling reagents 43-45 and their taurine derivatives 46-48.
FIG. 12 shows the synthesis of compound 44.
FIG. 13A shows the synthesis of compound 63,
FIG. 13B shows the synthesis of compound 68,
and FIG. 13C shows the synthesis of compound 71.
FIG. 14 shows the synthesis of labeling reagent 74 and its taurine derivative 75.

DETAILED DESCRIPTION OF INVENTION

Figure 15A:
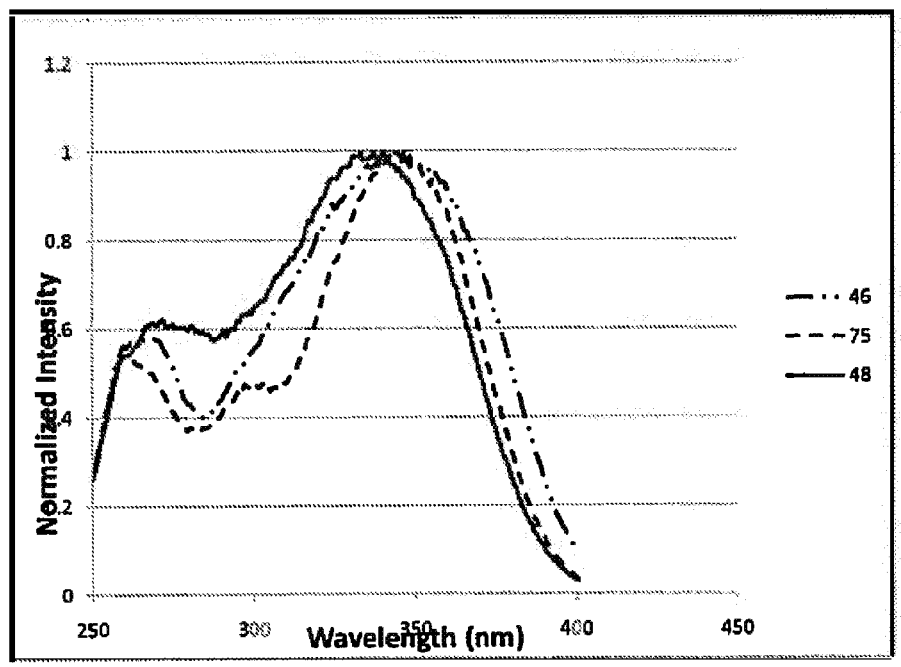
FIG. 15A shows the excitation maxima of chelates 46, 48, and 75.

The aim of the present invention is to provide means to obtain improved lanthanide chelate labels to be used in specific bioaffinity based binding assays, such as immunoassays (both homogeneous and heterogeneous), nucleic acid hybridization assays, receptor-binding assays, enzymatic assays, immunocytochemical, immunohistochemical assays and cell based assays utilizing fluorometric or time-resolved fluorometric determination of specific luminescence. Chelates of the present invention provide means to obtain unproved bioaffinity based binding assays related to e.g. assay sensitivity, kinetics and background.

Luminescent Lanthanide Chelate

One aspect of the present invention relates to a luminescent lanthanide chelate of the formula (I)

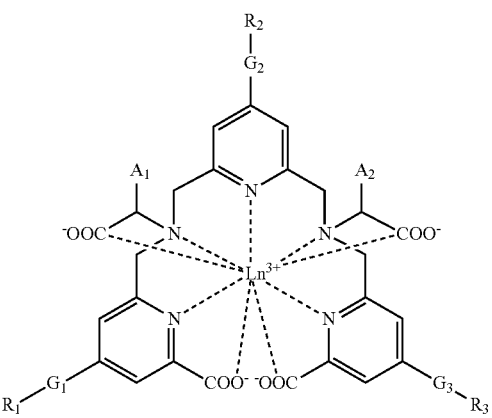

wherein
each of $G_1$, $G_2$, and $G_3$ is independently selected from i) a conjugating group and ii) a single bond, provided that at least one of $G_1$, $G^2$ and $G_3$ is independently a conjugating group, in particular two or all three of $G_1$, $G_2$ and $G_3$ are independently a conjugating group;
each $R_1$, $R_2$ and $R_3$ is independently selected from i) a reactive group Z. ii) a hydrophilic group, and iii) hydrogen, or the respective group, $R_1$, $R_2$, and $R_3$, is absent;
each of $A_1$ and $A_2$ is independently selected from i) a reactive group Z, ii) a hydrophilic group, and iii) hydrogen or $C_{1-6}$-alkyl;
wherein at least one of $R_1$, $R_2$, $R_3$, $A_1$ and $A_2$ is a reactive group Z, and
$Ln^{3+}$ is a lanthanide ion.

At least one of the groups $G_1$, $G_2$ and $G_3$ is a conjugating group. In such instances, such conjugating groups, $G_1$, $G_2$, and/or $G_3$, are groups conjugated with the pyridines. These groups may be substituted with various groups to improve water solubility and/or to shift excitation wavelength and/or to enhance molar excitation coefficient. Any group of $G_1$, $G_2$ and $G_3$ not being a conjugating group simply represents a single bond between the pyridine and $R_1$, $R_2$ or $R_3$, respectively.

In one interesting embodiment at least two of $G_1$, $G^2$ and $G_3$ are independently a conjugating group.

In the currently most interesting embodiments, each $G_1$, $G^2$ and $G_3$ is independently a conjugating group.

In some embodiments, the conjugating group consists of one, two or three moieties, each moiety being selected from ethenylene (—CH=CH—), ethynediyl (—C≡C—), carbonyl (—C(=O)—), and biradicals of (hetero)aromatic ring or ring systems (-Het/Ar-), e.g. phenylene biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene, and oxadiazolylene.

The groups are arranged so as to be conjugated with each other and are attached to the respective pyridine in such a way that the conjugating group is conjugated with the pyridine.

Each of the biradicals of (hetero)aromatic ring or ring systems (-Het/Ar-) may be unsubstituted, mono-$R_4$-substituted, di-$R_4,R_5$-substituted, tri-$R_4,R_5,R_6$-substituted, tetra-$R_4,R_5,R_6,R_7$-substituted, or penta-$R_4,R_5,R_6,R_7,R_8$-substituted, wherein each of such possible substituents R4, R5, R6, R7 and R8 independently are selected from $C_{1-12}$-alkyl, —$(CH_2)_{0-6}COOH$, —$(CH_2)_{0-6}COO^-$, —$(CH_2)_{0-6}SO_3^-$, —$NHC(=O)R_{10}$, —$NCH_3C(=O)R_{10}$, —$C(=O)NHR_{10}$, —$C(=O)NCH_3R_{10}$, —$NCH(=O)NHR_{10}$, —$NHC(=S)NHR_{10}$, —$C(=O)R_{10}$, —F, —Cl, —Br, —I, hydroxyl (—OH), mercapto (—SH), —$OR_9$, —$SR_9$, and a hydrophilic group, and wherein $R_9$ is selected from —$CF_3$, —$C_{1-12}$-alkyl, —$(CH_2)_{1-6}COOH$, —$(CH_2)_{1-6}COO^-$, —$(CH_2)_{1-6}SO_3H$, —$(CH_2)_{1-6}SO_3^-$, —$NHC(=S)NHR_{10}$, —$NCH_3C(=O)R_{10}$, —$C(=O)NHR_{10}$, —$C(=O)NCH_3R_{10}$, $NHC(=O)NHR_{10}$, —$NHC(=S)NHR_{10}$, —$C(=O)R_{10}$ and a hydrophilic group, wherein $R_{10}$ is selected from $C_{1-12}$-alkyl, —$(CH_2)_{1-6}COOH$, —$(CH_2)_{1-6}COO^-$, —$(CH_2)_{1-6}SO_3H$, —$(CH_2)_{1-6}SO_3^-$ and a hydrophilic group.

With different R groups the excitation wavelength can be shifted to longer wavelength, which together with high molar absorptivity (ε) means that the labels could be excited by cheap and small LEDs instead of expensive devices presently in use.

In one interesting embodiment, two of $G_1$, $G_2$ and $G_3$, in particular all three, are independently selected from phenylethynyl ($C_6H_5$—C≡C—), phenyl, thienyl and furyl, such as phenylethynyl, thienyl and furyl, in particular from phenylethynyl, which each may be substituted (cf. as described above for the biradicals of (hetero)aromatic ring or ring systems).

Each of $R_1$, $R_2$, and $R_3$ is independently selected from i) a reactive group Z, ii) a hydrophilic group, and iii) hydrogen. In the event that the biradicals of (hetero)aromatic ring or ring systems constituting $G_1$, $G_2$ and $G_3$, or a part of $G_1$, $G_2$ and $G_3$, is fully substituted, the respective group, $R_1$, $R_2$, and $R_3$, is absent.

Each of $A_1$ and $A_2$ is independently selected from i) a reactive group Z, ii) a hydrophilic group, and iii) hydrogen or $C_{1-6}$-alkyl, in particular from i) a reactive group Z, ii) a hydrophilic group, and iii) hydrogen.

At least one reactive group is required in the chelate molecule. Typically, the number of Z groups in the chelate molecule is 1, 2, or 3, in particular 1 or 2, more preferably just 1.

The reactive group Z is facilitating the labelling of a biospecific binding reactant, or is facilitating the formation of a covalent bond to a solid support material. In case the chelate has a polymerizing group as reactive group, then the chelate may be introduced in the solid support, e.g. a particle, simultaneously with the preparation of the particles.

Examples of the reactive group are those selected from azido (—$N_3$), alkynyl (—C≡CH), alkylene (—CH=$CH_2$), amino (—$NH_2$), aminooxy (—O—$NH_2$), carboxyl (—COOH), aldehyde (—CHO), mercapto (—SH), maleimido groups or activated derivatives thereof, including isocyanato (—NCO), isothiocyanato (—NCS), diazonium (—$N^+N$), bromoacetamido, indoacetamido, reactive esters, pyridyl-2-dithio, and 6-substituted 4-chloro-1,3,5-triazin-2-ylamino. In two examples, the reactive group comprises an isothiocyanato (—NCS) group.

The substituents in 6-substituted 4-chloro-1,3,5-triazin-2-ylamino can be selected from the group consisting hydrogen, halogen, alkoxy, aryloxy, ammo alkyl with one to six carbon atoms, substituted amino or thioethers, and preferable selected from the group consisting of chloro, fluoro, ethoxy, 2-methoxyethoxy, 2-cyanoethoxy, 2,2,2-trifluoroethoxy, thiophenoxy or ethoxycarbonyl-thiomethoxy. The substituted amino or thioether is preferable mono- or disubstituted each substituent being preferable independently selected from the group consisting of an alkyl or alkoxy with one to six carbon atoms, phenyl, carbonyl or carboxyl.

It follows that upon reaction with a biospecific binding reactant (see further below), the reactive group Z establishes a link to said biospecific binding reactant, e.g. of one of the following types: a thiourea (—NH—C(=S)—NH—), an aminoacetamide (—NH—CO—$CH_2$—NH—), an amide (—NH—CO—, —CO—NH—, —$NCH_3$—CO— and —CO—$NCH_3$—), and aliphatic thioether (—S—), a disulfide (—S—S—), a 6-substituted-1,3,5-triazine-2,4-diamine, a

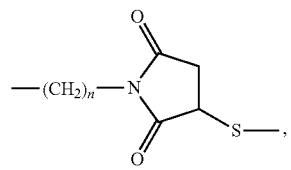

wherein n=1-6; and a triazole (e.g. formed by the so-called "click" chemistry).

When present, any hydrophilic groups are present in order to, e.g., improve water solubility of the chelate.

Examples of hydrophilic groups are mono- and oligosaccharides, such as monosaccharides and disaccharides, oligoalkylene glycols (e.g. those having 1-20 repeating units) such as oligoethylene glycol and oligopropylene glycol, etc.

In one embodiment, the hydrophilic group is selected from monosaccharides, disaccharides, —$(CH^2)_{1-3}$—O—$(CH_2CH_2O)_{0-5}$—H, —$(CH_2)_{1-3}$—O—$(CH_2CH_2O)_{0-5}$—$C_{1-4}$-alkyl, —O—$(CH_2CH_2O)_{1-6}$—H, and —O—$(CH_2CH_2O)_{1-6}$—$C_{1-4}$-alkyl, in particular monosaccharides.

In the present context, the term "monosaccharide" is intended to mean $C_5$-$C_7$ carbohydrates being either in the acyclic or in cyclic form. Examples of monosaccharides are $C_6$ carbohydrates, e.g. those selected from

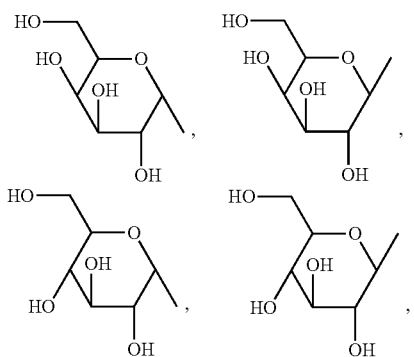

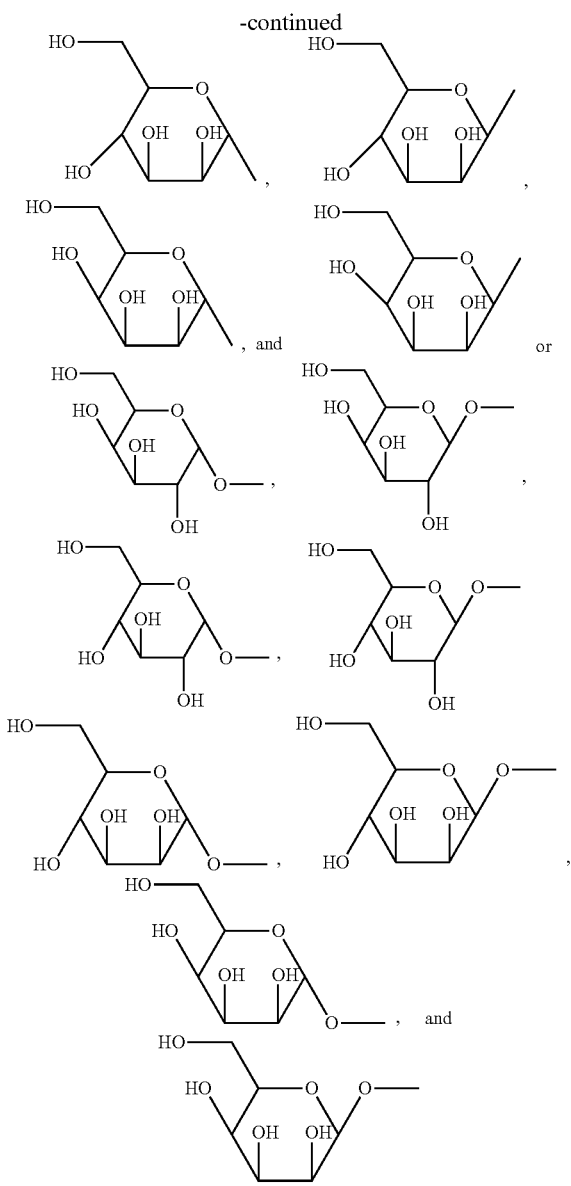

In the present context, the term "disaccharide" is intended to mean two monosaccharides (cf. above) linked together, preferably via glycosidic bonds.

It should be understood that when any of $R_1$, $R_2$, $R_3$, $A_1$, and $A_2$ designates a reactive group Z, the group Z may include a spacer, i.e. a distance-making biradical, so as—if necessary or desirable—to position the reactive group Z in a position accessible for reaction with the biospecific binding reactant. Similarly, when any of $R_1$, $R_2$, $R_3$, $A_1$, and $A_2$ designates a hydrophilic group, the hydrophilic group may include a spacer. In both instances, the spacer may be readily introduced in the course of the synthesis of the ligand or the chelate. As an example which can easily be generalized (and with reference to Example 3), the reaction between compound 4 and the glycine ethyl ester, it would be possible to use another a-amino acid with a functional side chain (e.g. (protected) glutamic or aspartic acid or protected omitine or lysine) so as to provide a part of a spacer for establishing a reactive group or a hydrophilic group having included a spacer. An example is given in FIG. 8.

The term "spacer" is intended to mean a distance-making group between, e.g., a conjugating group or a pyridine moiety of the core structure and, e.g. the reactive group Z or a hydrophilic group. The spacer typically has a length of 1-20 bonds between the attachment point and reactive group (or hydrophilic group), such as 3-15 bonds, or 5-12 bonds. The said spacer is formed of one to five moieties, each moiety selected from the group consisting of phenylene, alkylene containing 1-10 carbon atoms, an ethynediyl (—C≡C—), an ether (—O—), a thioether (—S—), a disulfide (—S—S—), an amide (—C(=O)—NH—, —NH—C(=O)—, —C(=O)—NCH$_3$— and —NCH$_3$—C(=O)—), a thiourea (—NH—C(=S)—NH—) and a triazole. An example of such a spacer having 11 bonds is illustrated in FIG. 8.

In one embodiment, the hydrophilic group (if present) comprises a spacer which is a distance-making radical, wherein the spacer is as defined above.

In another embodiment, the reactive group Z comprises a spacer which is a distance-making radical, wherein the spacer is as defined above.

In some embodiments, at least one of -$A_1$ and -$A_2$ is —H, in particular both of -$A_1$ and -$A_2$ are —H.

In other embodiments, at least one of -$A_1$ and -$A_2$ is not —H, in particular one of $A_1$ and $A_2$ is a reactive group (Z) connected via a spacer, for example —(CH$_2$)$_2$—CO—NH—(CH$_2$)$^2$—C$_6$H$_4$—NCS.

In still another embodiment, at least one of -$A_1$ and -$A_2$ is not —H, in particular one of $A_1$ and $A_2$ is a hydrophilic group, optionally connected via a spacer.

The term "lanthanide ion" or "$Ln^{3+}$" is intended to mean a trivalent ion of the lanthanide series of the Periodic Table of Elements, e.g. europium(III), terbium(III), samarium(III) and dysprosium(III), i.e. $Eu^{3+}$, $Tb^{3+}$, $Sm^{3+}$ or $Dy^{3+}$. In many embodiments, europium(III) ($Eu^{3+}$) and terbium(III) ($Tb^{3+}$) are preferred.

It should be understood that the basic structure lanthanide chelate of the formula (I) (as well as the lanthanide chelating ligand of the formula (II); see further below) comprises at least four negative charges, and even more negative charges if some substituents are of the type —COO$^{31}$ or —SO$_3^-$). Hence, it should be understood that the lanthanide chelate and the lanthanide chelating ligand, respectively, in addition to what is illustrated in formula (I) and formula (II) are further associated with one or more cations as counter ions. Examples of such counter ions are Na$^+$, Ca2$^+$, K$^+$. Particularly preferred are Na$^+$ and K$^+$. Preferably, the counter ions are those from Groups IA and IIA of the periodic table of elements.

Moreover, the invention provides highly luminescent labels for all lanthanides which provides multi-label possibilities Lanthamide Chelating Ligand Hence, another aspect of the present invention relates to a lanthanide chelating ligand of the formula (II),

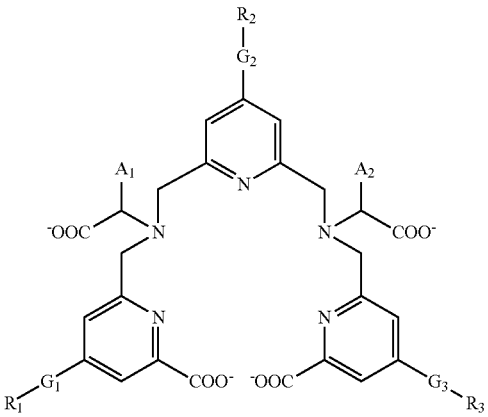

and wherein each of G1, G2, G3, R1, R2, R3, A1 and A2 represents the groups G1, G2, G3, R1, R2, R3, A1 and A2 as defined for formula (I).

If the ligand is to be used in peptide or oligonucleotide synthesis as a means to prepare a labeled peptide or a labeled oligonucleotide as described in e.g. US 2005/0181393, it is preferable to use one functional group for attaching the ligand to the peptide's or oligonucleotide's back-bone during the synthesis in $R_1$, $R_2$, $R_3$, $A_1$ or $A^2$ as described in US 2005/0181393.

Preferred Embodiments

In some preferred embodiments, the chelate molecule comprises a single reactive group Z, in particular as the substituent $R_2$, e.g. —NCS.

In further embodiments, -$G_2$—$R_2$ is a -ethynylene-phenylene-$R_2$ wherein $R_2$ is a reactive group, e.g. —NCS.

In some preferred embodiments, the lanthanide chelate of formula (I) is one wherein each of $G_1$, $G_2$ and $G_3$ is phenylethynyl, each of -$A_1$ and -$A_2$ is —H, each of $R_1$ and $R_3$ is a hydrophilic group, such as a monosaccharide, e.g.

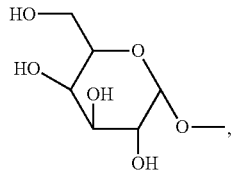

and $R_2$ is a reactive group, e.g, —NCS.

In another embodiment, the lanthanide chelate of formula (I) is one wherein each of $G_1$ and $G_3$ are 3,5-bis(carboxymethoxy)phenylethynyl and $G_2$ is phenylethynl, each of -$A_1$ and -$A_2$ is —H, each of $R_1$ and $R_3$ is —H, and $R_2$ is a reactive group, e.g. —NCS.

In still another embodiment, the lanthanide chelate of formula (I) is one wherein each of $G_1$, $G_2$ and $G_3$ is phenylethynyl, one of -$A_1$ and -$A_2$ is —H, and the other of -$A_1$ and -$A_2$ is a reactive group including a spacer, e.g. —(CH$_2$)$_2$—CO—NH—(CH$_2$)$_2$—C$_6$H$_4$—NCS, and each of $R_1$, $R_2$ and $R_3$ is a hydrophilic group, such as a monosaccharide, e.g.

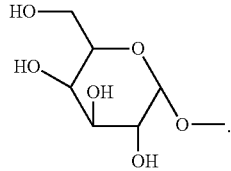

In still another embodiment, the lanthanide chelate of formula (I) is one wherein each of $G_1$ and $G_3$ are 4-(carboxymethylthio)phenylethynyl and $G_2$ is phenylethynyl, each of -$A_1$ and -$A_2$ is —H, each of $R_1$ and $R_3$ is —H, and $R_2$ is a reactive group, e.g. —NCS.

In still another embodiment, the lanthanide chelate of formula (I) is one wherein each of $G_1$ and $G_3$ are 2,4-bis(carboxymethylthio)phenylethynyl and $G_2$ is phenylethynyl, each of -$A_1$ and -$A_2$ is —H, each of $R_1$ and $R_3$ is —H, and $R_2$ is a reactive group, e.g. —NCS.

In another embodiment, the lanthanide chelate of formula (I) is one wherein each of $G_1$ and $G_3$ are 2,4,6-tris(carboxymethoxy)phenylethynyl and G2 is phenylethynyl, each of -$A_1$ and -$A_2$ is —H, each of $R_1$ and $R_3$ is —H, and $R_2$ is a reactive group, e.g. —NCS.

In another embodiment, the lanthanide chelate of formula (I) is one wherein each of $G_1$ and $G_3$ are furan-2-yl and $G_2$ is phenylethynyl, each of -$A_1$ and -$A_2$ is —H, each of $R_1$ and $R_3$ is —H, and $R_2$ is a reactive group, e.g. —NCS.

In another embodiment, the lanthanide chelate of formula (I) is one wherein each of $G_1$ and $G_3$ are thien-2-yl and $G_2$ is phenylethynyl, each of -$A_1$ and -$A_2$ is —H, each of $R_1$ and $R_3$ is —H, and $R_2$ is a reactive group, e.g. —NCS.

In another embodiment, the lanthanide chelate of formula (I) is one wherein each of $R_1$—$G_1$ and $R_3$—$G_3$ are (2,4-di(NaOOC—CH$_2$—O—)phenyl)ethynyl, $G_2$ is (2-(NaOOC—CH$_2$—O—) phenyl)ethynyl, each of -$A_1$ and -$A_2$ is -H, and $R_2$ is a reactive group, e.g. —NCS.

In these embodiments, the lanthanide ion ($Ln^{3+}$) is preferably selected from $Sm^{3+}$ and $Eu^{3+}$, in particular $Eu^{3+}$.

The corresponding lanthanide chelating ligands of the formula (II) are equally interesting. The lanthanide chelating ligand is especially suitable for use in peptide synthesis, oligonucleotide synthesis and for solid supports.

A Detectable Molecule

Still another aspect of the present invention relates to a detectable molecule comprising a biospecific binding reactant conjugated to a luminescent lanthanide chelate as defined hereinabove. Conjugation is typically obtained by means of a reactive group of said chelate.

The biospecific binding reactant should be capable of specifically binding an analyte of interest for the purpose of quantitative or qualitative analysis of said analyte in a sample.

Examples of biospecific binding reactants are those selected from an antibody, an antigen, a receptor ligand, a specific binding protein, a DNA probe, a RNA probe, an oligopeptide, an oligonucleotide, a modified oligonucleotide (e.g. an LNA modified oligonucleotide), a modified polynucleotide (e.g. an LNA modified polynucleotide, a protein, an oligosaccharide, a polysaccharide, a phospholipid, a PNA, a steroid, a hapten, a drug, a receptor binding ligand, and lectine.

In a preferred embodiment, the biospecific binding reactant is selected from antibodies, e.g. Troponin I antibodies (anti-TnI).

A Method for Carrying Out a Biospecific Binding Assay

A still further aspect of the invention relates to a method of carrying out a biospecific binding assay, wherein the method comprises the steps of:

a) forming a biocomplex between an analyte and a biospecific binding reactant labelled by lanthanide chelate as defined herein;
b) exciting said biocomplex with radiation having an excitation wavelength, thereby forming an excited biocomplex;
and c) detecting emission radiation emitted from said excited biocomplex.

The method follows the conventional assay steps as will be evident for the skilled person.

This being said, a further aspect of the invention relates to the use of a detectable molecule as defined above in a specific bioaffinity based binding assay utilizing time-resolved fluorometric determination of a specific luminescence. In one embodiment, the specific bioaffinity based binding assay is a heterogeneous immunoassay, a homogenous immunoassay, a DNA hybridization assay, a receptor binding assay, an im immunocytochemical or an immunohistochemical assay.

A Solid Support

Still another aspect of the invention relates to a solid support material conjugated with a luminescent lanthanide chelate as defined hereinabove. The luminescent lanthanide chelate is typically immobilized to the solid support material either covalently or non-covalently.

In some interesting embodiments, the solid support material is selected from a nanoparticle, a microparticle, a slide, a plate, and a solid phase synthesis resin.

The novel nine-dentate lanthanide chelates ligands and the corresponding luminescent lanthanide chelates and labeled biospecific binding reactant are based on an open chain, i.e. acyclic, ligand structure with three chromophores which provides surprisingly efficiently excitation of the chelated lanthanide ion. At the same time, all important features of the luminescent lanthanide chelate and labeled biospecific binding reactant can be retained without any additional tbrmation of aggregates and purification problems, The chelates of the present invention aim to combine several important features in a single label such as:
(a) high absorptivity, preferable over 50,000 $cm^{-1}$ at suitable wavelength, preferable over 300 nm,
(b) three separate UV absorbing parts (chromophores, triplet sensitizer) in the same ligand structure to allow the high absorptivity of the reactant,
(c) effective energy transfer from the chromophores to the lanthanide ion,
(d) a nine dentate chelating completely protection of the chelated ion against and the well-known luminescence quenching of water molecules,
(e) a strongly chelating part to create i) thermodynamic stability required for storing the labeled reactants for extended period of time, and ii) high kinetic stability to allow the labeled reactants to be used in conditions where competing metal ions or chelating agents may be present,
(f) functional groups to allow high water solubility, to prevent formation of aggregated during labeling of biomolecules and unspecific binding of labeled biomolecules, and to allow the UV excitation over 300 nm and high absorptivity,
(g) optimal amount of $CH_2$ groups in the close vicinity of the emittive lanthanide ion. Thus, the non-radiative quenching of the ion luminescence through C—H bond vibrational energy manifolds is less significant to offer enhanced luminescence, and
(h) with europium chelates the ligand field with the invented chelate emphasizes the emission line intensity at ca 615 nm over the other emissions lines to offer enhanced luminescence.

EXAMPLES

The following non-limiting examples are aimed to further demonstrate the invention. The structures and synthetic routes employed are presented in FIGS. 1-14. One key synthesis step is to use so called Sonogashira reaction to prepare the conjugated triple bond structures. It is obvious for any person skilled in the art to use known synthetic Stille and Suzuki methods described e.g. in Bioconjugate Chem., 20 (2009) 404 and references situated herein to prepare the e.g. phenyl, thienyl or furyl based lanthanide chelates according to the present invention.

$^1$H-NMR spectra were recorded with Bruker AVANCE DRX 500 MHz. Tetramethyl silane was used as internal reference. Mass spectra were recorded either on Applied Biosystems QSTAR XL ESI-TOF instrument or PerSeptive Biosystems Voyager DE-PRO MALDI-TOF instrument using a-cyano-4-cinnamic acid matrix. UV-Vis spectra were recorded on Pharmacia Ultrospec 3300 pro. Fluorescence efficiencies were determined with Perkin-Elmer Wallac Victor platefluorometer. Luminescence decay times, excitation and emission spectra as well as fluorescence lifetimes were measured using Varian Cary Eclipse spectrofluorometer. Column chromatography was performed with columns packed with silica gel 60 (Merck).

Example 1

Synthesis of 2,6-bis(hydroxymethyl)-4-iodopyridine (2)

Diethyl 4-iodo-2,6-pyridinedicarboxylate (1) (5.57 g, 17.3 mmol) was suspended in ethanol (130 ml). Sodium borohydride (2.95 g, 78 mmol) was added in small portions to the stirred solution during 15 min. The mixture was refluxed for 1h 30 min and allowed then to cool down to RT. The reaction mixture was evaporated to dryness and the residue was suspended in saturated aqueous sodium hydrogen carbonate (35 ml). The suspension was rapidly boiled up, allowed to cool and evaporated to dryness. The residue was suspended in mixture of DMF and dichloromethane (1 : 1, 65 ml), filtrated through Celite pad and the filtrate was evaporated to dryness. The product was crystallized from water and dried in vacuum desiccator over silica gel. Yield 3.37 g (60%), $^1$HNMR (CDCl$_3$, δ ppm): 7.70 (2H, s), 5.46 (2H, s), 4.48 (4H, s), Compound 1 was prepared as described in Takalo H. and Kankare J., *Acta Chemica Scandinavica* B 41, 1987, 219-221.

Example 2

Synthesis of 2,6-bis(bromomethyl)-4-iodopyridine(3)

Phosphorus tribromide (2.45 ml, 26 mmol) was added drop-wise to anhydrous DMF (19.5 ml) at 0° C. resulting in a semisolid mixture. 2,6-bis(hydroxymethyl)-4-iodopyridine (2) (3.36 g, 12.7 mmol) was added to the mixture in small portions. The solid mixture solubilizes during the addition. The mixture was allowed to warm up to RT and stirred 4 h at RT. The reaction mixture was poured to 100 ml of aqueous sodium hydrogen carbonate (5%). The precipitated product was collected by filtration, washed with water and dried in vacuum desiccator over silica gel. Yield 4.51 g (91%). $^1$HNMR (CDCl$_3$, δ ppm): 7.76 (2H, s), 4.45 (4H, s)

Example 3

Synthesis of Compound ethyl-2-((4-bromo-6-(carboxyethyl)-pyridine-2-yl) methylenenitrilo)acetate (5)

4-promo-6-bromomethyl-2-carboxyethylpyridine (4) (2.99 g, 9.3 mmol) and glycine ethyl ester hydrochloride (6.52 g, 46.7 mmol) were dissolved in mixture of anhydrous acetonitrile (125 ml) and di-isopropylethylamine (16.5 ml). Mixture was stirred overnight at RT. Reaction mixture was evaporated to dryness and the product was purified with column chromatography using silica as a stationary phase and dichloromethane:methanol (97:3) as an eluent. Yield 2.78 g (86%). $^1$HNMR: (CDCl$_3$, δ ppm): 8.14 (1H, d, J=1.65 Hz), 7.85 (1H, d, J=1.60 Hz), 4.47 (2H, q, J=7.12 Hz), 4.20

(2H, q, J=7.13 Hz), 4.05 (2H, s), 3.47 (2H, s), 2.26 (1H, s), 1.43 (3H, t, J=7.13 Hz), 1.28 (3H, t, J=7.13Hz).

Compound 4 was prepared as described in Takalo et al., *Helv. Chim. Acta,* 1996, 79, 789-802.

Example 4

Synthesis of diethyl 6,6'-(((((4-iodopyridine-2,6-diyl) bis(methylene))bis((2-ethoxy-2-oxoethyl) azanediyl))bis(methylene))bis(4-bromopicolinate) (6)

Compound 3 (0.94 g, 2.4 mmol) and compound 5 (1.66 g, 4.8 mmol) were dissolved in anhydrous acetonitrile (80 ml). Anhydrous potassium carbonate (1.67 g, 12 mmol) was added and the mixture was stirred 4 hours at 55-60° C. Reaction mixture was allowed to cool down to RT and filtrated through Celite pad. The filtrate was evaporated to dryness and the product was purified with column chromatography using silica as a stationary phase and dichloromethane:methanol (95:5) as an eluent. Yield 1.57 g (71%). $^1$HNMR: (CDCl$_3$, δ ppm): 8.12 (2H, d, J=1.60 Hz), 8.07 (2H, d, J=1.40 Hz), 7.76 (2H, s), 4.46 (4H, q, J=7.12 Hz), 4.18 (4H, q, J=7.13), 4.08 (4H, s), 3.92 (4H, s), 3.49 (4H, s), 1.42 (6H, t, J=7.13), 1.28 (6H, t, J=7.13). MS(ESI-TOF) calculated for $C_{33}H_{38}Br_2IN_5O_8$ [M+H]$^+$: 918.02, found: 917.92

Example 5

Synthesis of diethyl 6,6'-(((((4-((4-aminophenyl) ethynyl)pyridine-2,6-diyl) bis(methylene))bis((2-ethoxy-2-oxoethyl)azanediyl)) b is (methylene)) bis(4-bromopicolinate) (7)

Compound 6 (412 mg, 0.45 mmol) was dissolved in anhydrous dichloromethane (6 ml). Triethylamine (2 ml), copper (I) iodide (3.2 mg, 0.017 mmol), bis(triphenylphosphine)palladium(II) dichloride (9.5 mg, 0.014 mmol) and 4-ethynylaniline (52.5 mg, 0.45 mmol) were added. The reaction mixture was deaerated with argon and the mixture was stirred 3 h at RT. Reaction mixture was evaporated to dryness and the product was purified with column chromatography using silica as a stationary phase and dichloromethane: methanol (90:10) as an eluent. Yield 193 mg (47%). $^1$HNMR: (CDCl$_3$, δ ppm): 8.11 (2H, d, J=1.35 Hz), 7.83 (2H, s), 7.32 (2H, d, J=8.15 Hz), 7.18 (2H, s), 6.67 (2H, d, J=8.45 Hz) 4.38 (4H, s), 4.30 (4H, q, J=6.74 Hz), 4.01 (4H, q, J=7.10 Hz), 3.97 (4H, s), 3.39 (4H, s), 1.32 (6H, t, J=6.90Hz), 1.17 (6H, t, J=6.93 Hz). MS(ESI-TOF) calculated for $C_{41}H_{44}Br_2N_6O_8$ [M+H]$^+$: 907.17, found: 907.05

Example 6

Synthesis of diethyl 6,6'-(((((4-((4-aminophenyl) ethynyl) pyridine-2,6-diyl) bis(methylene))bis((2-ethoxy-2-oxoethyl)azanediyl))bis(methylene))bis((4-(4-(2,3,4,6-tetra-o-acetyl-α-galactopyranoxy) phenyl)ethynyl)picolinate) (9):

Compound 7 (190 mg, 0.21 mmol) and compound 8 (240 mg, 0.54 mmol) were dissolved in anhydrous tetrahydrofuran (3 ml). Triethylamine (3 ml), copper (I) iodide (2.3 mg, 0.012 mmol), bis(triphenylphosphine)palladiuin(II) dichloride (4.3 mg, 0.006 mmol) (63.8 mg, 0.54 mmol) were added. The reaction mixture was deaerated with argon and the mixture was stirred overnight at 55-60° C. Reaction mixture was evaporated to dryness and the product was purified with column chromatography using silica as a stationary phase and dichloromethane: methanol (90:10) as an eluent. Yield 155 mg (44%). MS(ESI-TOF) calculated for $C_{85}H_{90}N_6O_{28}$ [M+H]$^+$: 1643.59, found: 1643.51

Example 7

Synthesis of 6,6'-(((4-((4-aminophenyl)ethynyl) pyridine-2,6-diyl) bis(methylene))bis((carboxylatomethyl)azanediyl))bis(methylene))bis((4-(4-α-galactopyranoxy) phenyl)ethynyl)picolinate europium. (10)

Compound 9 (152 mg, 0.092 mmol) was dissolved in 0.5 KOH in ethanol (7.7 ml) and water was added (3.6 ml). The mixture was stirred at RT for 2 h. The mixture was evaporated to dryness, the residue was dissolved in water (2.5 ml) and pH was adjusted to 6.5 by addition of hydrochloric acid (6M). Europium chloride (34 mg, 0.092 mmol) dissolved in water (920 µl) was added to the reaction mixture. Reaction mixture was stirred at RT for 2 hours and. the pH was maintained at 6.3-6.5 by addition of sodium hydrogen carbonate or hydrochloric acid to the mixture. The product precipitated out from the reaction mixture and was isolated by centrifuggation. The product was dried overnight in vacuum desiccator over silica gel. Yield 115 mg. MS(ESI-TOF) calculated for $C_{61}H_{54}EuN_6O_{20}$-[M+2H]$^+$: 1345.28, found: 1345.25 UV/VIS: $\lambda_{max,abs}$ (H$_2$O)331 nm.

Example 8

Synthesis of 6,6'-(((((4-(4-isothiocyanatophenyl) ethynyl)pyridine-2,6-diyl) bis(methylene))bis((carboxylatomethyl)azanediyl))bis(methylene))bis((4-(4-α-galactopyranoxy)phenyl)ethynyl)picolinate europium (11)

Aqueous solution of compound 10 (108 mg, 0.08 mmol) was added to a mixture of thiophosgene (42 µl, 0.55 mmol), NaHCO$_3$ (52 mg, 0.61 mmol) and chloroform (1.65 ml). After stirring of 1 h at RT, the aqueous phase was washed with chloroform (3×1 ml). The pH was then adjusted to 6.8-7.2 with 1M acetic acid and the product was precipitated with acetone (33 ml). The product was collected by centrifugation, the precipitate was washed. with acetone (3×30 ml) and dried overnight in vacuum desiccator over silica gel. MS(ESI-TOF) calculated for $C_{62}H_{52}EuN_6O_{20}S^-$ [M−] 1385.22, found 1385.98. UV/VIS: $\lambda_{max,abs}$ (H$_2$O)=328 nm, $\epsilon$=86000 mol$^{-1}$ cm$^{-1}$

Example 9

Synthesis of 1-Bromo-3,5-dihydroxybenzene (13)

1-bromo-3,5-dimethoxybenzene (12) (1.00 g, 4.60 mmol) was dissolved in dry dichloromethane (40 ml) and cooled in an ice bath. Boron tribromide (1.33 ml, 13.82 mmol.) was added and the mixture was stirred on 2 h. The mixture was allowed to warm up to room temperature and stirred overnight. Methanol (1.4 ml) was added drop-wise to terminate the reaction, and the mixture was poured into water (50 ml) and stirred at RT for 2 h. Reaction mixture was neutralized with NaHCO$_3$ and the mixture extracted twice with ethyl acetate (30 ml). Combined organic layers were dried over Na$_2$SO$_4$ and evaporated to dryness. Product was purified by column chromatography using silica gel as stationary phase and methanol:dichloromethane (5:95) as eluent. Product was a white solid. Yield: 0.71 g (81%). $^1$HNMR (DMSO-d6, δ ppm): 9.68 (2H, s) 638 (2H, d, J=2 Hz), 6.19 (1H, dd, J -2 Hz).

Example 10

Synthesis of di-tert-buty 2,2'-((5-bromo-1,3-phenylene)bis(oxy))diacetate (14)

Compound 13 (0.49 g, 2.59 mmol) was dissolved in DMF (10 ml, dry). Anhydrous $K_2CO_3$ (2.15 g, 15.56 mmol) and tert-butyl bromoacetate (1.15 ml, 7.78 mmol) were added and the mixture was stirred overnight under argon atmosphere at 50° C. Water (17 ml) was added and the mixture was extracted with ethyl acetate (3×40 ml). Combined organic extracts were dried over $NaHCO_3$ and evaporated to dryness. Crude product was purified by column chromatography using silica gel as stationary phase and dichloromethane as eluent. Product was a white solid. Yield: 0.95 g (87%) $^1$H NMR ($CDCl_3$, δ ppm): 6.67 (2H, d, J=2 Hz), 6.42 (1H, dd, J=2 Hz), 1.49 (18H, s)

Example 11

Synthesis of di-tert-butyl 2,2'-((5-((trimethylsilyl)ethynyl)-1,3-phenylene) bis(oxy))diacetate (15)

Compound 14 (2.00 g, 4.79 mmol) was dissolved in DMF (4 ml, dry) and the solution was placed in a microwave reaction vial. Diethyl amine (12 ml, dry), $Pd(PPh_3)_2Cl_2$ (168 mg, 0.24 mmol), CuI (46 mg, 0.24 mmol) and $PPh_3$ (251 mg, 0.96 mmol) were added and the vial was sealed in an argon atmosphere. Trimethylsilyl acetylene (996 μl, 7.19 mmol) was added through a septum and the mixture was stirred at 120° C. for 30 minutes using microwave heating. Reaction mixture was evaporated to dryness, dissolved in dichloromethane and purified by column chromatography using silica gel as stationary phase and ethyl acetate:petroleum ether (10:90) as eluent. Yield: 1.36 g (65%) $^1$H NMR ($CDCl_3$, δ ppm): 6.61 (2H, d, J=2.35 Hz), 6.49 (1H, dd, J=2.3 Hz), 4.46 (4H, s), 1.49 (18H, s), 0.23 (9H, m).

Example 12.

Synthesis of di-tert-butyl 2,2'-((5-ethynyl-1,3-phenylene)bis(oxy))diacetate (16)

Compound 15 (1.29 g, 2.98 mmol) was dissolved in dichloromethane (40 ml, dry). Tetrabutyl ammoniuin fluoride (0.934 g, 3.57 mmol) was added and the mixture was stirred in argon atmosphere at room temperature for 45 min. Mixture was washed with 10% citric acid solution (20 ml), and four times with water (4×40 ml). The organic phase was dried over $Na_2SO_4$ and evaporated to dryness. Crude product was purified by column chromatography using silica gel as stationary phase and ethyl acetate: petroleum ether (10: 90) as eluent. Product was a yellowish solid. Yield: 895 mg (83%). $^1$H NMR ($CDCl_3$, δ ppm): 6.64 (2H, d, J=2.3 Hz), 6.51 (1H, dd, J=2.33 Hz), 4.47 (4H, s), 3.02 (1H, s), 1.49 (18H, s).

Example 13.

Synthesis of tetra-bert-butyl 2,2',2'',2'''-(((((6,6'-((((4-((4-aminophenyl) ethynyl)pyridine-2,6-diyl)bis(methylene))bis((2-ethoxy-2-oxoethyl) azanediyl))bis(methylene))bis(2-(ethoxy carbonyl) pyridine-6,4-diyl))bis(ethyne-2,1-diyl)) bis(benzene-5,3,1-triyl))tetrakis(oxy))tetraacetate (17)

Compound 16 (0.167 g, 0.459 mmol) and compound 7 (0.167 g, 0.184 mmol) were dissolved in mixture of anhydrous tetrahydrofurane (4 ml) and triethylamine (2.5 ml). Bis(triphenylphosphine)palladium(II) dichloride (3.8 mg, 0.0054 mmol) and copper (I) iodide (2.3 mg, (0.012 mmol) were added and the mixture was stirred overnight under argon atmosphere at 55-60° C. Reaction mixture was evaporated to dryness and purified by column chromatography using silica gel as stationary phase and methanol:dichloromethane (10:90) as eluent. Yield: 71 mg (27%) MS(ESI-TOF) calculated for $C_{81}H_{94}N_6O_{20}$ [M+H]$^+$: 1471.66, Found: 1471.68

Example 14

Synthesis of 6,6'-(((((4-((4-aminophenyl)ethynyl) pyridine-2,6-diyl) bis(methylene))bis((carboxylatomethyl)azanediyl))bis(methylene))bis(4-((3,5-bis (carboxymethoxy)phenyl)ethynyl)picolinate europium(III) (18)

Compound 17 (68 mg, 0.048 mmol) was dissolved in trifluoroacetic acid (1 ml, 13.5 mmol) and the mixture was stirred at RT for 1.51 h. Reaction mixture was evaporated to dryness without heating. Diethyl ether (2.5 ml) was added to the residue and the mixture was stirred for 15 minutes. Product precipitated from the mixture and was isolated by centrifugation. The precipitate was washed twice with diethyl ether and then dried in vacuum desiccator over silica gel. Dried precipitate (64 mg, 0.051 mmol) was dissolved in the mixture of water (1.8 ml) and 0.5 M potassium hydroxide solution in ethanol (4 ml). Mixture was stirred in RT for 2 h. Reaction mixture was evaporated to dryness and the residue was dissolved in water (1.7 ml). pH was adjusted to 6.5 by addition of hydrochloric acid (6 M). Europium chloride (20 mg, 0.055 mmol) dissolved in water (485 μl) was added to the reaction mixture drop-wise. Reaction mixture was stirred at RT for 2 hours and the pH was maintained at 6.3-6.5 by addition of sodium hydrogen carbonate to the mixture. Excess of europium was precipitated from the mixture by adjusting pH to 8.5-9.0 by addition of sodium hydroxide and the precipitate was removed by centrifugation. The product was precipitated with acetone (25 ml) and isolated by centrifugation. The precipitate was washed with acetone (3×10 ml) and dried overnight in vacuum desiccator over silica gel. Yield: 180 mg. MS(ESI-TOF) calculated for $C_{57}H_{142}EuN_6O_{20}$ [M+2H] (for free acids without sodium ions): 1285.18, Found: 1285.24

Example 15

Synthesis of 6.6'-(((((4-((4-isothiocyanatophenyl) ethynyl)pyridine-2,6-diyl) bis(methylene))bis((carboxylatomethyl)azanediyl))bis(methylene))bis(4-((3, 5-bis (carboxymethoxy)phenyl)ethynyl)picolinate) europium(III) (19)

Aqueous solution of compound 18 (175 mg, 0.143 mmol) was added drop-wise to a 5 mixture of chloroform (2.85 ml), thiophosgene (74 µl, 0.97 mmol) and sodium hydrogen carbonate (91 mg, 1.09 mmol). Reaction mixture was stirred at RT for 45 min. The two phases were separated and the aqueous phase was washed with chloroform (3×6 ml). pH was adjusted to 7 with 1M acetic acid and the product was precipitated with acetone (57 ml) and isolated by centrifugation. The precipitate was washed with acetone (3×15 ml) and dried overnight in vacuum desiccator over silica gel. Yield: 216 mg. MS(ESI-TOF) calculated for $C_{58}H_{40}EuN_6O_{20}S''$ $[M-H]^{2-}$ (for free acids without sodium ions): 662.56, Found: 662.47

Example 16

Comparison between luminescence of Eu-chelate according to present invention and a conventional 9-dentate α-galactose Eu chelate Compound 11 (5.3 mg) and a conventional 9-dentate α-galactose Eu chelate (21)(5.5 mg) were coupled to taurine (5 mg for each reaction) by dissolving the starting materials in to a mixture of aqueous sodium hydrogen carbonate (2 ml, 50 mM, pH9.8) and DMF (200 µl). The mixtures were incubated overnight at RT. The products (20 and 22) were purified by using reversed phase HPLC (RP-18 column). The solvents were A: Triethyl ammonium acetate buffer (20 mM, pH7) and B: 50% acetonitrile in triethyl ammonium acetate buffer (20 mM, pH7). The gradient was started from 5% of solvent B and the amount of solvent B was linearly raised to 100% in 25 minutes. The products eluted from the column at 16.7 min (20) and at 15.1 min (22) time points. Fractions containing the products were collected, pooled and evaporated to dryness.

The conventional 9-dentate α-galactose Eu chelate (21) was prepared according to von Lode P. et al., *Anal. Chem.*, 2003, 75, 3193-3201.

The purified products Were dissolved in water and analyzed for UV spectrum, Eu-content with DELFIA® against Eu standard material and luminescence signal in water with Victor™ Plate fluorometer. In the luminescence measurements the concentrations of compounds 20 and 22 were adjusted equimolar based on the Eu content. The results are summarized in Table 1.

TABLE 1

|  | Compound 22 (reference compound) | Compound 20 |
|---|---|---|
| Molar absorptivity (ε) based on Eu content | 56,000 | 86,000 |

TABLE 1-continued

|  | Compound 22 (reference compound) | Compound 20 |
|---|---|---|
| Relative luminescence signal (concentration approx. 1 nM) | 195,000 | 633,000 |

These results show that Compound 20 provides surprisingly high luminescence yield compared to the reference compound (more than 300% higher). Earlier published luminescence field (εΦ) for α-gal-9-D Eu (compound 21) coupled to antibody was 4,787 (von Lode P. et al., *Anal. Chem.*, 2003, 75, 3193-3201). By assuming the same luminescence yield for compound 22 the luminescence yield for compound 20 can be estimated to be: εΦ=633,000/195,000× 4,787=approx. 15,500. That is one of the highest luminescence yield ever seen with a chelate having also a reactive group for labeling a biomolecule.

Example 17

Labelling of Antibody with Compound 19

Labelling of an TnI antibody was performed as described in von Lode P. et al., *Anal. Chem.*, 2003, 75, 3193-3201 by using 90 fold excess of compound 19. The reactions were carried out overnight at RT. Labelled antibody was separated from the excess of compound 19 on Superdex 200 HR 10/30 gel filtration column (GE healthcare) by using Tris-saline-azide (Tris 50 mM, NaCI 0.9%, pH 7.75) buffer as an eluent. The fractions containing the antibody were pooled and the europium concentration was measured against Eu standard material with Victor™ plate fluorometer. The labelling degree of 1.6 Eu/IgG was obtained.

Example 18

Troponin I Immunoassay

The TnI antibody labeled with compound 19 was tested in sandwich immunoassay for cardiac troponin I. As a reference compound a TnI antibody labelled with compound 21 (labelling degree 11 Eu/IgG) was used. 10 µl of diluted tracer antibody (5 ng/µl) and 20 pi of TnI standard solution were pipetted to a pre-coated assay well (single wells in 96 well plate format, wells coated with streptavidin and a biotinylated capture antibody against TnI, Innotrac Diagnostics). The reaction mixtures were incubated 20 min at 36° with shaking. The wells were washed 6 times and dried prior to measurement with Victor™ Plate fluorometer. The results are summarized in Table 2. Both A and B standards were measured in 12 replicates and other standards C—F in 6 replicates.

TABLE 2

|  |  | cTnI std (ng/ml) | A 0 | B 0.022 | C 0.08 | D 0.75 | E 5.34 | F 41.6 |
|---|---|---|---|---|---|---|---|---|
| IgG labeled with compound 19 | cps-blank |  | 197 | 310 | 1030 | 9098 | 64347 | 459222 |
| reference compound | cps-blank |  | 195 | 258 | 775 | 6624 | 47913 | 369540 |
| IgG labeled with compound 19 | cv % |  | 7.8 | 6.4 | 4.1 | 3.2 | 1.9 | 3.2 |
| reference compound | cv % |  | 9.5 | 8.7 | 3.8 | 3.1 | 5.3 | 7.1 |

The results show that compound 19 provides the same signal levels with 1/10 amount of chelate/IgG when compared to the reference compound (21). In other words the compound according to present invention provides an order of magnitude more luminescence signal per chelate than the state of the art reference compound.

Remarks

The chelate is nine-dentate (optimal for lanthanides) and has three separate chromophores which should give 50% higher luminescence compared to the present nine-dentate chelates in use having two separate chromophores. Compared to other known chelates with two or three chromophores (e.g. NOTA and DOTA based structures) the invented chelate has less $CH_2$ groups in the close vicinity of the emitting ion. Thus the non-radiative quenching of the ion luminescence through C—H bond vibrational energy manifolds is less significant and thus the luminescence should be more enhanced. Moreover, being acyclic nine-dentate chelate the ligand do not have any sterical hindrance when complexing a lanthanide ion. In that case the distance between the emitting lanthanide ion and pyridine nitrogen is optimal 1) for effective energy transfer from the donor pyridine nitrogen to the lanthanide ion and 2) for high complex stability, and thus offer enhanced luminescence. The chelate synthesis is easier to be performed compared to the other three chromophores containing DOTA based chelates. The three chromophores between each other can be entirely different which means more possible variations and more tailoring possibilities e.g solubility in different solvents, various excitation wavelengths and energy transfers etc. Cheap and small LEDs can be used to excite the labelled biomolecules. Thus, smaller and cheaper instrumentation for commercial bioassay systems can be used. The ligand field with the invented chelate emphasizes the emission line intensity at approx. 615 nm over the other emissions lines, and thus the observed luminescence should be improved compared to others. Increased chromophoric symmetry is expected to increase luminescence yield.

Surprisingly, the observed luminescence was approx. 300% higher compared to the present chelates in use. The assumption was an approx. 50-70% improvement. This means that it should be possible to improve our assay sensitivities approx. three-fold compared to the present sensitivities.

Example 19

Synthesis of triethyl 2,2',2"-((4-iodo-1,3,5-phenylene)tris(oxy))triacetate (23)

A mixture of 4-Iodo-1,3,5-trihydroxybenzene (3.41 g, 13.5 mmol; Acta Chem. Scand. 1991, 45, 539), dry $K_2CO_3$ (6.17 g, 44.7 mmol), ethyl bromoacetate (4.96 ml, 44.7 mmol) and dry MeCN (100 ml) was stirred overnight at 55° C. The mixture was filtered, the solid material washed with MeCN and the filtrate was evaporated to dryness. The product was purified by column chromatography using silica gel as stationary phase and MeOH:$CH_2Cl_2$ (first 0:100, then 20:80) as eluent. Yield: 0.64 g (9%). $^1$H NMR (CDCl$_3$, δ ppm): 6.10 (2H, s), 4.65 (4H, s), 4.55 (4H, s), 4.27 (2H, q, J=7.15 Hz), 4.26 (4H, q, J=7.15 Hz), 1.31 (3H, t, J=7.15 Hz), 1.30 (6H, t, J=7.15 Hz). MS(ESI-TOF) calculated for $C_{18}H_{23}IO_9$ [M+H]$^+$: 511.05, found: 510.93.

Example 20

Synthesis of triethyl 2,2',2"-((4-(trimethylsilyl)ethynyl-1,3,5-phenylene) tris(oxy))-triacetate (24)

This compound 24 was synthesized from the compound 23 using a method analogous to the synthesis described in the Example 11. The mixture was stirred first at 100° C. for 30 minutes, then at 120° C. for 20 minutes by using microwave heating. The mixture was extracted with $Et_2O$ (50 ml), washed with $H_2O$ (2×20 ml), dried with $Na_2SO_4$, and the product purified by column chromatography using silica gel as stationary phase and ethyl acetate:petroleum ether (first 20:80, then 30:70) as eluent. Yield: 70%. $^1$H NMR (CDCl$_3$, δ ppm): 6.10 (2H, s), 4.67 (4H, s), 4.55 (2H, s), 4.27 (2H, g, J=7.15 Hz), 4.26 (4H, q, J=7.15 Hz), 1.30 (6H, t, J=7.15 Hz), 1.29 (3H, t, J=7.15 Hz), 0.26 (9H, s). MS(ESI-TOF) calculated for $C_{23}H_{32}O_9Si$ [M+H]$^+$: 481.19, found: 481.99.

Example 21

Synthesis of triethyl 2,2',2"-((4-ethynyl-1,3,5-30 phenylene)tris(oxy))triacetate (25)

This compound 25 was synthesized from the compound 24 using a method analogous to the synthesis described in the Example 12. After washings with 10% citric acid and $H_2O$, the product (100%) was used for the next step without further purifications. $^1$H NMR (CDCl$_3$, δ ppm): 6.06 (2H, s), 4.69 (4H, s), 4.55 (2H, s), 4.27 (2H, q, J=7.15 Hz), 4.26 (4H, q, J=7.15 Hz), 3.50 (1H, s), 1.30 (3H, t, J=7.15 Hz), 1.29 (6H, t, J=7.15 Hz), MS(ESI-TOF) calculated for $C_{20}H_{24}O_9$ [M+]$^+$: 409.15, found: 409.20.

Example 22

Synthesis of diethyl 2,2'-(1,3-phenylenebis(sulfanediyl))diacetate (26)

A mixture of benzene-1,3-dithiol (0.76 g, 4 mmol), dry $K_2CO_3$ (2.21 g, 16 mmol) ethyl bromoacetate (0.93 ml, 8.4 mmol) and dry MeCN (20 ml) was stirred overnight at 55° C. and under agron. The mixture was filtered, the solid material washed with MeCN and the filtrate was evaporated to dryness. The product was purified by column chromatography using silica gel as stationary phase and $CH_2Cl_2$ as eluent. Yield: 0.96 g (76%). $^1$H NMR (CDCl$_3$, δ ppm): 7.45-7.43 (1H, m), 7.25-7.20 (3H, m), 4.18 (4H, q, J=7.15 Hz), 3.64 (4H, s), 1.23 (6H, t, J=7.15 Hz). MS(ESI-TOF) calculated for $C_{14}H_{18}O_4S_2$ [M+H]$^+$: 315.07, found: 315.98.

Example 23

Synthesis of diethyl 2,2'-(4-bromo-1,3-phenylenebis (sulfanediyl))-15 diacetate (27)

A mixture of the compound 26 (0.64 g, 2.04 mmol) and N-bromosuccinimide (0.47 g, 2.66 mmol) in $CH_2Cl_2$ (10 ml) was stirred for four days at room temperature. After evaporation to dryness, the product was purified by column chromatography using silica gel as stationary phase and petroleum ether: $CH_2Cl_2$ (20:80) as eluent. Yield: 0.50 g (63%). $^1$H NMR (CDCl$_3$, δ ppm): 7.45 (1H, d, J=8.32 Hz), 7.42 (1H, d, J=2.18 Hz), 7.09 (1H, dd, J=8.32 and 2.18 Hz), 4.20 (2H, q, J=7.15 Hz), 4.18 (2H, q, J=7.15 Hz), 3.70 (2H, s), 3.63 (2H, s), 1.27 (3H, t, J=7.15 Hz), 1.24 (3H, t, J=7.15 Hz). MS(ESI-TOF) calculated for $C_{14}H_{17}BrO4S_2$ [M+H]$^+$: 394.98 and 391.99, found: 394.95 and 391.82.

Example 24

Synthesis of diethyl 2,2'-(4-(trimethylsilyl)ethynyl-1,3-phenylenebis (sulfanediyl))-diacetate (28)

This compound 28 was synthesized from the compound 27 using a method analogous to the synthesis described in the Example 11. The mixture was stirred at 100° C. for 30 minutes by using microwave heating. After evaporation to dryness, the product was purified by column chromatography using silica gel as stationary phase and ethyl acetate: petroleum ether (first 10:90, then 20:80) as eluent. Yield: 82%. $^1$H NMR (CDCl$_3$, δ ppm): 7.36 (1H, d, J=1.75 Hz), 7.34 (1H, d, J=8.08 Hz), 7.12 (1H, dd, J=8.08 and 1.75 Hz), 4.19 (2H, q, J=7.13 Hz), 4.18 (2H, q, J=7.13 Hz), 3.73 (2H, s), 3.67 (2H, s), 1.26 (3H, t, J=7.13 Hz), 1.24 (3H, t, J=7.13 Hz), 0.27 (9H, s). MS(ESI-TOF) calculated for $C_{19}H_{26}O_4S_2Si$ [M+H]$^+$: 411.11, found: 412.02.

Example 25

Synthesis of diethyl 2,2'-(4-ethynyl-1,3-phenylen-ebis(sulfanediyl))diacetate (29)

This compound 29 was synthesized from the compound 28 using a method analogous to the synthesis described in the Example 12. After washings with 10% citric acid and H$_2$O, the product was purified by column chromatography using silica gel as stationary phase and ethyl acetate:petroleum ether (first 10:90, then 15:85, and finally 20:80) as eluent. Yield: 41%. $^1$H NMR (CDCl$_3$, δ ppm): 7.40 (1H, d, J=1.88 Hz), 7.39 (1H, d, J=8.08 Hz), 7.15 (1H, dd, J=8.08 and 1.88 Hz), 4.19 (2H, q, J=7.15 Hz), 4.18 (2H, q, J=7.15 Hz); 3.73 (2H, s), 3.68 (2H, s), 3.47 (1H, s), 1.25 (6H, t, J=7.15 Hz). MS(ESI-TOF) calculated for $C_{15}H_{18}O_4S_2$ [M+H]$^+$: 339.07, found: 339.83.

Example 26

Synthesis of Ethyl 2-((4-bromophenyl)thio)acetate 30

A mixture of 4-bromothiophenol (0.95 g, 5 mmol), dry K$_2$CO$_3$ (1.38 g, 10 mmol), ethyl bromoacetate (0.72 ml, 6.5 mmol) and dry MeCN (20 ml) was stirred three days at room temperature and under agron. The mixture was filtered, the solid material washed with MeCN and the filtrate was evaporated to dryness. The product was purified by column chromatography using silica gel as stationary phase and ethyl acetate:petroleum ether as eluent (first 2:98. then 7:93). yield: 1.22 g (88%). $^1$H NMR (CDCl$_3$, δ ppm): 7.42 (2H, d, J=8.58 Hz), 7.28 (2H, d, J=8.58 Hz), 4.17 (2H, q, J=7.15 Hz), 3.61 (2H, s), 1.23 (3H, t, J=7.15 Hz). MS(ESI-TOF) calculated for $C_{10}H_{11}BrO^2S$ [M+H]$^+$: 276.97 and 274.98, found: 276.66 and 274.63.

Example 27

Synthesis of ethyl 2-((4-((trimethylsilyl)ethynyl)phenyl)thio)acetate 31

This compound 31 was synthesized from the compound 30 using a method analogous to the synthesis described in the Example 11. The mixture was stirred at 120° C. for 40 minutes by using microwave heating. After evaporation to dryness, the product was purified by column chromatography using silica gel as stationary phase and ethyl acetate: petroleum ether (10:90) as eluent. Yield: 88%. $^1$H NMR (CDCl$_3$, δ ppm): 7.38 (2H, d, J=8.38 Hz), 7.30 (2H, d, J=8.38 Hz) 4.17 (2H, q, J=7.15 Hz), 3.64 (2H, s), 1.23 (3H, t, J=7.15 Hz), 0.24 (9H, s). MS(ESI-TOF) calculated for $C_{15}H_{20}O_2SSi$ [M+H]$^+$: 294.11, found: 294.11.

Example 28

Synthesis of ethyl 2-((4-ethynylphenyl)thio)acetate 32

This compound 32 was synthesized from the compound 31 using a method analogous to the synthesis described in the Example 12. After washings with 10% citric acid and H$_2$O, the product was purified by column chromatography using silica gel as stationary phase and ethyl acetate:petroleum ether (first 5:95, then 10:90) as eluent. Yield: 68%. $^1$H NMR (CDCl$_3$, δ ppm): 7.41 (2H, d, J=8.45 Hz), 7.32 (2H, d, J=8.45 Hz), 4.18 (2H, q, J=7.15 Hz), 3.65 (2H, s), 3.09 (1H, s), 1.23 (3H, t, J=7.15 Hz). MS(ESI-TOF) calculated for $C_{12}H_{12}O_2S$ [M+H]$^+$: 221.07, found: 221.15.

Example 29

Synthesis of N-(4-ethynylphenyl)-2,2,2-trifluoroacetamide (33)

4-Ethynylaniline (1.38 g, 11.8 mmol) was added in small portions into an ice-cold (CF$_3$CO)$_2$O (6.6 ml). After stirring for 10 min in ice-bath, the mixture was stirred for 2.5 hours at room temperature. The mixture was poured into ice-H$_2$O (100 ml), the product filtered and washed with H$_2$O. The product (2.29 g, 91%) was used for the next step without further purifications. $^1$H NMR (CDCl$_3$): δ (ppm)) 8.08 (1H, s), 7.55 (2H, d, J=8.80 Hz) 7.51 (2H, d, J=8.80 Hz), 3.1 (1H, s). MS(ESI-TOF) calculated for $C_{10}H_6F_3NO$ [M+H]$^+$: calculated 214.02, found 213.07.

Example 30

Synthesis of N-(4-((2,6-bis(hydroxymxymethyl)pyridin-4-yl)ethynyl)phenyl)-2.2.2-trifluoroacetamide (34)

A mixture of the compound 33 (0.55 g, 258 mmol) and 6-bromo-2,6-dihydroxymethylpyridine (0.47 g, 2.15 mmol; Acta Chem. Scand, 1988, Ser B, 42, 614) in dry triethylamine (5 ml) and tetrahydrfurane (10 ml) was de-aerated with argon. After addition of bis(triphenylphosphine)-palladium(II) chloride (30 mg, 43 μmol) and CuI (16 mg, 86 μmol), the mixture was stirred for 19 hours at 55° C. After evaporation to dryness, the residue was treated. with a cold mixture of CH$_2$Cl$_2$ (40 ml) and H$_2$O (20 ml), filtered and the product (0.56 g, 75%) washed with cold H$^2$O (10 ml) and CH$_2$Cl$_2$(10 ml). Yield: 0.56 g (75%). $^1$H NMR (D6-DMSO, δ ppm): 11.4 (1H, bs), 7.79 (2H, d, J=8.80 Hz), 7.68 (2H, d, J=8.80 Hz) 7.42 (2H, s), 5.49 (2H, bs), 4.56 (4H, s). MS(ESI-TOF) calculated for $C_{17}H_{13}F_3N_2O_3$ [M+H]$^+$: calculated 351.10, found 351.96.

Example 31

Synthesis of N-(4-((2,6-bis(bromomethyl)pyridin-4-yl)ethynyl)phenyl)-2.2.2-trifluoroacetamide (35)

PBr3 (225 μl) was added in a suspension of the compound 34 (0.56 g, 1.6 mmol) in CHCl$_3$ (65 ml). After stirring for 20 hours at 60° C., the mixture was neutralized with 5% NaHCO$_3$ (35 ml). The aqueous phase was extracted with CHCl$_3$ (40 ml) and the combined organic phases were dried with Na$_2$SO$_4$, filtered and evaporated to dryness. The product (1.09 g, 93%) was used for the next step without further purifications. $^1$H NMR (CDCl$^3$, δ ppm): 7.93 (1H, s), 7.63

(2H, d, J=8.68 Hz), 7.59 (2H, J=8.68 Hz), 7.47 (2H, s), 4.53 (4H, s), MS(ESI-TOF) calculated for $C_{17}H_{11}Br_2F_3N_2O$ [M+H]$^+$: calculated 474.93, 476.93, 498.92, found 475.38, 477.44, 479.45.

Example 32

Synthesis of diethyl 6,6'-((((4-((4-trifluoroa cetami-dophenyl)ethynyl)pyridine-2,6-diyl) bis(methylene)) bis((2-ethoxy-2-oxoethyl) azanediyl))bis(methyl-ene))bis(4-bromopicolinate) (36)

This compound 36 was synthesized from the compounds 34 and 5 using a method analogous to the synthesis described in the Example 4. Reaction time at 70° C. was 27 hours. The product was purified by column chromatography using silica gel as stationary phase and triethylamine:ethyl acetate:petroleum ether (1:69:30) as eluent. Yield: 66%. $^1$H NMR (CDCl$^3$, δ ppm): 8.53 (1H, s), 8.14 (2H, d, J=1.80 Hz), 8.11 (2 H, d, J=1.80 Hz), 7.68 (2 H, d, J=8.73 Hz), 7.60 (2H, d, J=8.73 Hz), 7.34 (2H, s), 4.44 (4H, q, J=7.08 Hz), 4.18 (4 H, q, J=7.15 Hz); 4.10 (4H, s), 3.98 (4 H, s), 3.50 (4 H, s), 1.40 (6H, t, J=7.08 Hz), 1.28 (6H, t, J=7.15 Hz), MS(ESI-TOF) calculated for $C_{43}H_{43}Br_2F_3N_6O_9$ [M+]$^+$: calculated 1003.15, 1005.15, 1007.15, found 1003.71, 1005.48, 1007.58.

Example 33

Synthesis of the Compound 37

A mixture of the compound 36 (120 g, 0.148 mmol) and 25 (145 mg, 0.355 mmol) in dry triethylamine (1 ml) and tetrahydrofurane (2 ml) was de-aerated with argon. After addition of bis(triphenylphosphine)palladium(II) chloride (10 mg, 14 μmol) and CuI (6 mg, 28 μmol), the mixture was stirred for 22 hours at 55° C. After evaporation to dryness, the residue was dissolved in CH$_2$Cl$_2$ (40 ml), washed with H$_2$O (3×10 ml) and dried with Na$_2$SO$_4$. The product was purified by column chromatography using silica gel as stationary phase and triethylamine:ethyl acetate:petroleum ether (1:69:30) as eluent. Yield: 115 mg (47%). $^1$H NMR (CDCl$_3$, δ ppm): 9.12 (1H, s), 8.09 (2H, d, J=1.25 Hz), 8.06 (2H, d, J=1.25 Hz), 7.57 (2 H, s), 7.34 (2H, J=8.80 Hz), 7.30 (2H, d, J=8.80 Hz), 5.97 (4H, s), 4.63 (8H, s), 4.60 (4H, s), 4.45 (4H, q, J=7.12 Hz), 4.30 (4H, q, J=7.12 Hz), 4.21 (8H, q, J=7.12 Hz), 4.17 (4H, q, J=7.12), 4.10 (4H, s), 4.02 (4H, s), 3.52 (4H, s), 1.42 (6H, t, J=7.12 Hz), 1.33 (6H, t, J=7.12 Hz), 1.29 (6H, J=7.12 Hz), 1.25 (12H, t, J=7.12 Hz). MS(ESI-TOF) calculated for $C_{83}H_{89}F_3N_6O_{27}$ [M+H]$^+$: calculated 1659.58, found 1659.81.

Example 34

Synthesis of the Compound 38

This compound 38 was synthesized from the compounds 36 and 29 using a method analogous to the synthesis described in the Example 33. The product was purified by column chromatography using silica gel as stationary phase and triethylamine:ethyl acetate:petroleum ether (1:69:30) as eluent. Yeild: 85%. $^1$H NMR (CDCl$^3$, δ ppm): 9.22 (1H, s), 8.07 (2H, d, J=1.15 Hz), 8.02 (2H, d, J=1.15 Hz), 7.55 (2H, s), 7.41 (2H, d, J=8.75 Hz), 7.38 (2H, d, J=8.10 Hz), 7.31 (2H, d, J=8.75 Hz), 7.30 (2H, d, J=1.67 Hz), 7.01 (2H, dd, J=8.10 and 1.67 Hz), 4.46 (4H, q, J=7.15 Hz), 4.22 (4H, q, J=7.15 Hz), 4.19 (4H, q, J=7.15 Hz), 4.17 (4H, q, J=7.15 Hz), 4.10 (4H, s), 3.89 (4H, s), 3.74 (4H, s), 3.70 (4H, s), 3.50 (4H, s), 1.42 (6H, t, J=7.15 Hz), 1.28 (12H, t, J=7.15 Hz), 1.24 (6H, t, J=7.15 Hz). MS(ESI-TOF) calculated for $C_{75}H_{77}F_3N_6O_{17}S_4$ [M+H]$^+$: calculated 1519.42, found 1519.56.

Example 35

Synthesis of the Compound 39

This compound 39 was synthesized from the compounds 36 and 32 using a method analogous to the synthesis described in the Example 33. The product was purified by column chromatography using silica gel as ationary phase and triethylamine:ethyl acetate:petroleum ether (1:69:30) as eluent. Yield: 81%. $^1$H NMR (CDCl$_3$, δ ppm): 9.29 (1H, s), 8.03 (2H, d, J=1.28 Hz), 8.01 (2H, d, J=1.18 Hz), 7.57 (2H, s), 7.44 (4H, d, J=8.48 Hz), 7.42 (2H, d, J=8.70 Hz), 7.32 (2H, d, J=8.70 Hz), 7.25 (4H, d, J=8.48 Hz), 4.46 (4H, q, J=7.15 Hz), 4.21 (4H, J=7.15 Hz), 4.18 (4H, q, J=7.15 Hz), 4.08 (4H, s), 3.95 (4H, s), 3.73 (4H, s), 3.49 (4H, s), 1.42 (6H, t, J=7.15 Hz), 1.28 (6H, t, J=7.15 Hz), 1.27 (6H, t, J=7.15 Hz).

Example 36

Synthesis of the Europium(III) Chelate 40

A mixture of the compound 37 (105 mg, 63 μmol) and 0.5M KOH in ethanol (9 ml) was stirred for 30 minutes at room temperature and water was added (2 ml). After stirring for 3 hours at room temperature, EtOH was evaporated, the residue was stirred for 30 minutes at room temperature, and the pH was adjusted to ca. 6.5 with 6M HCl. Europium(III) chloride (23 mg, 63 μmol) in H$_2$O (0.17 ml) was added within 10 minutes and the pH was maintained at 5-7 with solid NaHCO$_3$. After stirring for overnight at room temperature, the pH was raised to 8.5 with 1M NaOH, the precipitate was centrifuged off and the supernatant was extracted with phenol (once with 0.75 g and 3×0.5 g). The combined phenol phases were treated with H$_2$O (1 ml) and Et$_2$O (20 ml), the aqueous phase was washed with Et$_2$O (2×20 ml), and triturated with acetone. The precipitate was centrifuged and washed with acetone. The product was used for the next step without further purification. Conditions for HPLC run: see example 16. R$_f$(HPLC)=14.5 min. UV/VIS=359 nm.

Example 37

Synthesis of the Europium(III) Chelate 41

This compound 41 was synthesized front the compound 38 using a method analogous to the synthesis described in the Example 36. R$_f$(HPLC)=17.3 min. UV/VIS=318, 325 and 350 (sh) nm.

Example 38

Synthesis of the Europium(III) Chelate 42

This compound 42 was synthesized from the compound 39 using a method analogous to the synthesis described in the Example 36. R$_f$(HPLC)=21.5 min. UV/VIS=349 nm.

Example 39. Synthesis of the Europium(III) Labeling Chelate 43

This compound 43 was synthesized from the chelate 40 using a method analogous to the synthesis described in the

Example 40

Synthesis of the Europium(III) Labeling Chelate 44

This compound 44 was synthesized from the chelate 41 using a method analogous to the synthesis described in the Example 15. Conditions for HPLC run: see example 16. $R_f$(HPLC)=23.3 min. UV/VIS-=305 (sh), 318 and 335 (sh) nm.

Example 41

Synthesis of the Europium(III) Labeling Chelate 45

This compound 45 was synthesized from the chelate 42 using a method analogous to the synthesis described in the Example 15. Conditions for HPLC run: see example 16. $R_f$(HPLC)=27.9 min. UV/VIS=339 nm.

Example 42

Synthesis of the Europium(III) Chelate 46

This compound 46 was synthesized from the chelate 43 using a method analogous to the synthesis described in the Example 16. $R_f$(HPLC)=14.3 min. UV/VIS=349 nm.

Example 43

Synthesis of the Europium(III) Chelate 47

This compound 47 was synthesized from the chelate 44 using a method analogous to the synthesis described in the Example 16. $R_f$(HPLC)=17.2 min. UV/VIS=317 and 324 (sh) nm.

Example 44

Synthesis of the Europium(III) Chelate 48

This compound 48 was synthesized from the chelate 45 using a method analogous to the synthesis described in the Example 16. $R_f$(HPLC)=20.5 min. UV/VIS=336 nm.

Example 45

Synthesis of ethyl 2-((4-(furan-2-yl)-6-(carboxyethyl)-pyridine-2-yl) methylenenitrilo)-acetate 49

This compound 49 was synthesized from 4-(furan-2-yl)-6-bromomethyl-2-carboxyethylpyridine (WO2005/021538) using a method analogous to the synthesis described in the Example 3. The product was purified by column chromatography using silica gel as stationary phase and methanol:$CH_2CL_2$ (5:95) as eluent, $^1$H NMR ($CDCl_3$, δ ppm):8.21 (1H, d, J=1.43 Hz), 7.83 (1H, d, J=1.43 Hz), 7.58 (1H, d, J=1.63 Hz), 6.99 (1H, d, J=3.20 Hz), 6.55 (1H, dd, H=1.63 and 3.20 Hz), 4.49 (2H, q, J=7.12 Hz), 4.21 (2H, q, J=7.15 Hz), 4.08 (2H, s), 3.50 (2H, s), 2.37 (1 H, s) 1.45 (3H, t, J=7.12 Hz), 1.28 (3H, t, J=7.15 Hz). MS(ESI-TOF) calculated for $C_{17}H_{20}N_4O_5$ [M+]$^+$: calculated 333.15, found 334.09.

Example 46

Synthesis of ethyl 2-((4-(thiophen-2-yl)-6-(carboxyethyl)-pyridine-2-yl) methylenenitrilo)-acetate 50

This compound 50 was synthesized from 4-(thiophen-2-yl)-6-bromomethyl-2-carboxyethylpyridine (WO2005/021538) using a method analogous to the synthesis described in the Example 3. The product was purified by column chromatography using silica gel as stationary phase and methanol:$CH_2Cl_2$ (5:95) as eluent. $^1$H NMR ($CDCl_3$, δ ppm): 8.19 (1H, d, J=1.70 Hz), 7.79 (1H, d, J=1.70 Hz), 7.61 (1H, dd, J=1.05 and 3.70 Hz), 7.45 (1H, dd, J=1.05 and 5.05 Hz), 7.15 (1H, dd, J=3.70 and 5.05 Hz), 4.50 (2H, q, J=7.12 Hz), 4.20 (2H, q, J=7.15 Hz), 4.09 (2H, s), 3.51 (2H, s), 2.45 (1H, s), 1.45 (3H, t, J=7.12 Hz), 1.28 (3H, t, J=7.15 Hz). MS(ESI-TOF) calculated for $C_{17}H_{20}N_2O_4S$ [M+H]$^+$: calculated 349.11, found 349.99.

Example 47

Synthesis of diethyl 6,6'-((((4-bromopyridine-2,6-diyl) bis(methylene))bis((2-ethoxy-2oxoethyl) azanediyl))bis(methylene))bis(4-(fu ran-2-yl) picolinate) 51

A mixture of the compound 49 (0.16 g, 0.48 mmol), 2,6-dibromomethyl-4-bromopyridine (83 mg, 0.24 mmol; Acta Chem. Scand. 1988, Ser B, 42, 614), dry $K_2CO_3$ (0.13 g, 0.96 mmol) and dry MeCN (8 ml) was stirred for 4.5 hours at 55° C. The reaction mixture was filtered, the solid material washed with MeCN and the filtrate evaporated to dryness. The product was purified by column chromatography using silica gel as stationary phase and triethylamine: ethyl acetate:petroleum ether (1:69:30) as eluent. Yield: 0.19 g (95%) $^1$H NMR ($CDCl_3$, δ ppm): 8.18 (2H, d, J=1.38 Hz), 8.05 (2H, J=1.38 Hz), 7.70 (2H, s), 7.58 (2H, d, J=1.68 Hz), 6.98 (2H, d, J=3.42 Hz), 6.54 (2H, dd, J=1.68 and 3.42 Hz), 4.48 (4H, q, J=7.11 Hz), 4.17 (4H, J=7.12 Hz), 4.10 (4H, s), 3.96 (4H, s), 3.50 (4H, s), 1.44 (6H, t, J=7.11 Hz), 1.27 (6H, t, J=7.12 Hz). MS(ESI-TOF) calculated for $C_{41}H_{44}BrN_5O_{10}$ [M+H]$^+$: calculated 846.24 and 848.24, found 846.79 and 848.80.

Example 48

Synthesis of diethyl 6,6'-((((4-bromopyridine-2,6-diyl)bis(methylene))bis((2-ethoxy-2-oxoethyl) azanediyl))bis(methylene))bis(4-(thiophen-2-yl)picolinate) 52

This compound 52 was synthesized from the compound 50 using a method analogous to the synthesis described in the Example 47. The product was purified by column chromatography using silica gel as stationary phase and ethanol:$CH_2Cl_2$ (gradient from 2:98 to 15:85) as eluent. Yield: 50%. $^1$H NMR ($CDCl_3$, δ ppm): 8.15 (2H, s), 8.02 (2H, s), 7.71 (2H, s), 7.70 (2H, d, J=3.1 Hz), 7.42 (2H, J=4.8 Hz), 7.14 (2H, dd, J=3.1 and 4.8 Hz), 4.49 (4H, q, J=7.18 Hz), 4.18 (4H, q, J=7.07 Hz), 3.96 (4H, s), 3.96 (4H, s), 3.50 (4H, s), 1.43 (6H, t, J=7.18 Hz), 1.27 (6H, t, J=7.07 Hz).

MS(ESI-TOF) calculated for $C_{41}H_{44}BrN_5O_{10}S_2$ [M+H]$^+$: calculated 878.19 and 880.19, found 878.77 and 880.74.

Example 49

Synthesis of diethyl 6,6'-(((((4-((4-aminophenyl) ethynyl)pyridine-2,6-diyl) bis(methylene))bis((2-ethoxy-2-oxoethyl)azanediyl))bis(methylene))bis(4-(fu ran-2-yl) picolinate) 53

A mixture of the compound 51 (0.18 g, 0.21 mmol) and 4-ethynylanline (30 mg, 0.26 mmol) in dry triethylamine (1 ml) and tetrahydrofurane (2 ml) was de-aerated with argon. After addition of bis(triphenylphosphine)palladium(II) chloride (10 mg, 14 µmol) and CuI (6 mg, 28 µmol), the mixture was stirred for 20 hours at 55° C. After evaporation to dryness. The product was purified by column chromatography using silica gel as stationary phase and triethylamine: ethyl acetate:petroleum ether (first 1:69:30, then 1:79:20) as eluent. Yield: 0.14 g (74%). $^1$H NMR (CDCl$_3$, δ ppm): 8.18 (2H, d, J=1.20 Hz), 8.12 (2H, d, J=1.20 Hz), 7.74 (2H, s), 7.52 (2H, d, J=1.5 Hz), 7.32 (2H, d, J=8.48 Hz), 6.99 (2H, d, J=3.32 Hz), 6.65 (2H, d, J=8.48 Hz), 6.45 (2H, dd, J=1.5 and 3.32 Hz), 4.47 (4H, q, J=7.12 Hz), 4.17 (4H, q, J=7.12 Hz), 4.11 (4H, s), 3.98 (4H, s), 3.52 (4H, s), 1.43 (6H, t, J=7.12 Hz), 1.26 (6H, t, J=7.12 Hz), MS(ESI-TOF) calculated for $C_{49}H_{50}N_6O_{10}$ [M+H]$^+$: calculated 883.34, found 883.90.

Example 50

Synthesis of diethyl 6,6'-(((((4-((4-aminophenyl) ethynyl)pyridine-2,6-diyl) bis(methylene))bis((2-ethoxy-2-oxoethyl)azanediyl))bis(methylene))bis(4-10 (thiophen-2-yl) picolinate) 54

This compound 54 was synthesized from the compound 52 using a method analogous to the synthesis described in the Example 49. Yield: 50%. $^1$H NMR(CDCl$_3$, δ ppm): 8.14 (2H, s), 8.11 (2H, s), 7.61 (2H, d, J=3.40 Hz), 7.58 (2H, s), 7.30-7.33 (4H, m), 7.03-7.07 (2H, m), 8.35 (2H, d, J=8.35 Hz), 4.47 (4H, q, J=7.09 Hz), 4.18 (4H, q, J=7.10 15 Hz), 4.13 (4H, s), 3.98 (4H, s), 3.52 (4H, s), 1.41 (6h, t, J=7.09 Hz), 1.26 (6H, t, J=7.10 Hz). MS(ESI-TOF) calculated for $C_{49}H_{50}N_6O_8S_2$ [M+H]$^+$: calculated 915.32, found 915.05.

Example 51

Synthesis of Europium(III) Chelate 55

A mixture of the compound 53 (0.13 g, 0.143 mmol) and 0.5M KOH in ethanol (9 ml) was stirred for 30 minutes at room temperature and water was added (1 ml). After stirring for 3 hours at room temperature, EtOH was evaporated. After addition of H$_2$O (3 ml), the mixture was stirred for 3 hours at room temperature, and the pH was adjusted to ca. 6.5 with 6M HCl. Europium(III) chloride (52 mg, 0.143 mmol) in H2O (0.39 ml) was added within 10 minutes and the pH was maintained at 5-7 with solid NaHCO$_3$. After stirring for overnight at room temperature, the pH was raised to 8.5 with 1M NaOH. The solution was triturated with tetrahydrofurane, the precipitate centrifuged and washed with tetrahydrofurane. The product was used for the next step without further purification. Conditions for HPLC run: see example 16. R$_f$(HPLC)=24.9 min. UV/VIS=323 and 355 (sh) mm. MS(ESI-TOF) calculated for $C_{41}H_{30}EuN_6NaO_{10}$ [M+2H]$^+$ cal 944.13 found 945.73

Example 52

Synthesis of Europium(III) Chelate 56

This compound 56 was synthesized from the compound 54 using a method analogous to the synthesis described in the Example 51. Conditions for HPLC run: see example 16. Rf(HPLC)=26.3 min. UV/VIS=325 and 356 (sh) nm. MS(ESI-TOF) calculated for $C_{41}H_{30}EuN_6NaO_8S_2$ [M+2H]$^+$: calculated 976.09, found 976.88

Example 53

Synthesis of Europium(III) labeling dictate 57

This compound 57 was synthesized from the chelate 55 using a method analogous to the synthesis described in the Example 15. Conditions for HPLC run: see example 16. R$_f$(HPLC)=33.4. UV/VIS=325 nm. MS(ESI-TOF) calculated for $C_{42}H_{28}EuN_6NaO_{10}S$ [M+H]$^+$ calculated 985.08, found 984.77.

Example 54

Synthesis of Europium(III) Labeling Dictate 58

This compound 58 was synthesized from the chelate 56 using a method analogous to the synthesis described in the Example 15. Conditions for HPLC run: see example 16. R$_f$(HPLC)=34.7. UV/VIS=325 nm. MS(ESI-TOF) calculated for $C_{42}H_{28}EuN_6NaO_8S_3$ [M+H]$^+$ calculated 1017.04, found 1017.21.

Example 55

Synthesis of Europium(III) Chelate 59

This compound 59 was synthesized from the chelate 57 using a method analogous to the synthesis described in the Example 16. Conditions for HPLC run: see example 16. R$_f$(HPLC)=23.2. UV/VIS=321 nm.

Example 56

Synthesis of Europium(III) Chelate 60

This compound 60 was synthesized from the chelate 58 using a method analogous to the synthesis described in the Example 16. Conditions for HPLC run: see example 16. R$_f$(HPLC)=24.9. UV/VIS=322 nm.

Example 57

Synthesis of diethyl 2,2'-((4-bromo-1,3-phenylene) bis(oxy))diacetate (61)

4-bromoresorcinol (1.00 g, 5.29 mmol) was dissolved in DMF (20 ml, dry). Anhydrous K$_2$CO$_3$ (4.39 g, 31.74 mmol) and ethyl bromoacetate (2.30 ml, 15.87 mmol) were added. Mixture was stirred overnight at 40° C. under argon atmosphere. Water (30 ml) was added and the mixture was extracted with ethyl acetate (1×20 ml, 2×10 ml). Combined organic extracts were washed with water (2×10 ml), dried over Na$_2$SO$_4$ and concentrated. Crude product was purified by column chromatography using silica gel as stationary phase and dichloromethane as eluent. Product was a white solid. Yield: 1.70 g (89%) 1H NMR (CDCl3, δ ppm): 7.43 (1H, d, J=8.7 Hz), 6.48 (1H, d, J=2.7 Hz), 6.40 (1H, dd, J=2.7 Hz), 4.66 (2H, s), 4.57 (2H, s), 4.27 (4H, m) 1.30 (6H, m).

Example 58

Synthesis of diethyl 2,2'-((4-((trimethylsilyl)ethynyl)-1,3-phenylene) bis(oxy))diacetate (62)

Compound 61 (1.56 g, 4.33 mmol) was dissolved in DMF (3 ml, dry) and the solution was placed in a microwave reaction vial. Diethyl amine (9 ml, dry), $Pd(PPh_3)_2Cl_2$ (152.0 mg, 0.217 mmol), CuI (41.2 mg, 0.217 mmol) and $PPh_3$ (113.6 mg, 0.433 mmol) were added and the vial was sealed in an argon atmosphere. Trimethylsilyl acetylene (925 μl, 6.50 mmol) was added through a septum and the mixture was stirred at 100° C. for 30 minutes using microwave heating. Reaction mixture was filtrated through silica gel using dichloromethane as eluent and the filtrate was evaporated to dryness. The crude product was dissolved in dichloromethane and purified by column chromatography using silica gel as stationary phase and ethyl acetate:petroleum ether (10:90) as eluent. Yield: 0.99 g (61%). 1H NMR (CDCl3, δ ppm): 7.36 (1H, dd, J=1.35 Hz, J=7.55 Hz), 6.43 (2H, m), 4.67 (2H, s), 4.58 (2H, s), 4.27 (4H, m), 1.30 (6H, m), 0.25 (9H, s).

Example 59

Synthesis of diethyl 2,2'-((4-ethynyl-1,3-phenylene) bis(oxy))diacetate (63)

Compound 62 (398.9 mg, 1.054 mmol) was dissolved in dichloromethane (10 ml, dry). Tetrabutyl ammoniumfluoride (330.7 mg, 1.265 mmol) was added and the mixture was stirred in argon atmosphere at room temperature for 1 h 30 min. Mixture was washed with 10% citric acid solution (5 ml), and water (4×10 ml). The organic phase was dried over $Na_2SO_4$ and evaporated to dryness. Crude product was purified by column chromatography using silica gel as stationary phase and ethyl acetate:petroleum ether (15:85) as eluent. Yield 259.2 mg (80%). 1H NMR (CDCl3, δ ppm): 7.40 (1H, d, J=8.35 Hz), 6.45 (1H, d, J=2.4 Hz), 6.43 (1H, dd, J=5.25 Hz, J=2.4 Hz), 4.70 (2H, s), 4.59 (2H, s), 4.27 (4H, m) 3.24 (1H, s), 1.29 (6H, m).

Example 60

Synthesis of N-(4-bromo-3-methoxyphenyl)-2,2,2-trifluoroacetamide (64)

4-bromo-3-methoxyaniline (2.00 g, 9.90 mmol) was dissolved in THF (15 ml). The solution was added to ice cold trifluoroacetic anhydride (15 ml, 107.8 mmol) and the mixture was stirred 20 minutes on an ice-bath. Mixture was poured to ice water and stirring continued for 10 minutes. The mixture was extracted with dichloromethane (2×20 ml). Combined organic layers were washed with 5% $NaHCO_3$ (5×40 ml) and water (30 ml). Washed organic layers were dried on $Na_2SO_4$, filtered, and evaporated to dryness. The product (3.08, >99%) was used without further purifications.

Example 61

Synthesis of N-(4-bromo-3-hydroxyphenyl)-2,2,2-trifluoroacetamide (65)

Compound 65 was synthesized from compound 64 (3.08 g, 10 mmol) using method analogous to the synthesis in example 9. Yield 0.51 g (17%). $^1$H NMR (DMSO, δ ppm): 11.24 (1H, s), 10.51 (1H, s), 7.48 (2H, m), 7.05 (1H, dd, J=2.5 and 8.7 Hz).

Example 62

Synthesis of ethyl 2-(2-bromo-5-(2,2,2-trifluoroacetamido)phenoxy)acetate (66)

Compound 66 was synthesized from compound 65 (0.51 g, 1.78 mmol) using method analogous to the synthesis in example 10. $CH_3CN$ was used as solvent. Reaction time at 40° C. was 18 h. Yield 0.47 g (71%). $^1$H NMR (CDCl$_3$, δ ppm): 7.96 (1H, s), 7.52 (1H, d, J=8.5 Hz), 7.38 (1H, d, J=2.3 Hz), 6.91 (1H, dd, J=2.35 and 8.55 Hz), 4.72 (2H, s), 4.28 (2H, q, J=7.15 Hz), 1.32 (3H, t, J=7.15 Hz).

Example 63

Synthesis of ethyl 2-(5-(2,2,2-trifluoroacetamido)-2-((trimethylsilyl) ethynyl)phenoxy)acetate (67)

Compound 67 was synthesized from compound 66 (0.46 g, 1.24 mmol) using method analogous to the synthesis in example 11. Reaction time in the microwave at 100° C. was 30 minutes. Yield 0.37 g (77%). $^1$H NMR (CDCl$_3$, δ ppm): 7.92 (1H, s), 7.43 (1H, d, J=8.3 Hz), 7.34 (1H, d, J=1.9 Hz), 6.98 (1H, dd, J=1.9 and 8.3 Hz), 4.72 (2H, s), 4.29 (2H, q, J=7.15 Hz), 1.31 (3H, t, J=7.15 Hz), 0.26 (9H, s).

Example 64

Synthesis of ethyl 2-(2-ethynyl-5-(2,2,2-trifluoroacetamido)phenoxy)acetate (68)

Compound 68 was synthesized from compound 67 (0.37 g, 0.96 mmol) using method analogous to the synthesis in example 12 Yield 0.30 g (99%).

Example 65

Synthesis of ethyl 2-(2-((2,6-bis(hydroxymethyl) pyridin-4-yl)ethynyl)-5-(2,2,2-trifluoroacetamido) phenoxy)acetate (69)

Compound 69 was synthesized from compound 68 (0.37 g, 0.96 mmol) using method analogous to the synthesis in example 30. Yield 0.19 g (44%).

Example 66

Synthesis of ethyl 2-(2-((2,6-bis(bromomethyl)pyridin-4-yl)ethynyl)-5-(2,2,2-trifluoroacetamido) phenoxy)acetate (70)

Compound 70 was synthesized from compound 69 (0.19 g, 0.42 mmol) using method analogous to the synthesis in example 31. Yield 0.22 g (90%). $^1$H NMR (CDCl$_3$, δ ppm): 7.94 (1H, s), 7.51 (1H, d, J=8.3 Hz), 7.49 (2H, s), 7.44 (1H, d, J=1.85 Hz), 7.02 (1H, dd, J=1.9 and 8.3 Hz), 4.78 (2H, s), 4.53 (4H, s), 4.31 (2H, q, J=7.15 Hz) 1.33 (3H, t, J=7.15 Hz).

Example 67

Synthesis of diethyl 6,6'-((((4-((2-(2-ethoxy-2-oxoethoxy)-4-(2,2,2-trifluoroacetamido) phenyl)ethynyl)pyridine-2,6-diyl)bis(methylene))bis((2-ethoxy-2-oxoethyl)azanediyl))bis(methylene))bis(4-bromopicolinate) (71)

Compound 71 was synthesized from compound 70 (0.19 g, 0.42 mmol) and compound 5 (0.25 g, 0.73 mmol) using method analogous to the synthesis in example 4. Reaction time in 55° C. was 20 hours. Yield 0.23 g (57%). MS(MALDI) calculated for C$_{47}$H$_{49}$Br$_2$F$_3$N$_6$O$_{12}$ [M+H]$^+$: calculated 1107.18 found 1107.62.

Example 68

Synthesis of Compound 72

Compound 72 was synthesized from compound 71 (0.11 g, 0.10 mmol) and compound 63 (75 mg, 0.25 mmol) using method analogous to the synthesis in example 33. Yield 140 mg (87%)

Example 69

Synthesis of the Europium(III) Chelate 73

Compound 73 was synthesized from compound 72 (0.14 g, 0.09 mmol) using method analogous to the synthesis in example 36. The product was used for the next step without further purification. Conditions for HPLC run: see example 16. R$_f$(HPLC)=14.5 min. UV/VIS=350 nm.

Example 70

Synthesis of the Europium(III) Labeling Chelate 74

Compound 74 was synthesized from compound 73 (0.1 g, 0.07 mmol) using method analogous to the synthesis described in the Example 15. Conditions for HPLC run: see example 16. R$_f$(HPLC)=18.7 min. UV/VIS=340 nm.

Example 71

Synthesis of the Europium(III) Chelate 75

Compound 75 was synthesized from compound 74 using method analogous to the synthesis described in the Example 16. Conditions for HPLC run: see example 16. R$_f$(HPLC)= 14.5 min. UV/VIS=351 nm.

Example 72

Photo-Physical Properties of Novel Chelates Conjugated to Taurine (Chelates 19, 46, 47, 48, 59 and 75)

The prepared isothiocyante activated chelates (19, 43, 44, 45, 57 and 75) were conjugated to taurine as described above in Example 16. The products were purified with semi-preparative reversed phase HPLC (RP-18 column). After the product fractions were evaporated the residues were dissolved in 50 mM TRIS buffer.

The measured photo-physical properties excitation wavelengths ($\lambda_{exc}$), luminescence decay times (τ), molar absorptivities (ε), estimated luminescence yields (εΦ) of the novel chelates (19, 46, 48, and 59) in 50 mM TRIS buffer (pH 7.75) are in the Table 3.

TABLE 3

| Compound | ε/M$^1$cm$^{-1}$ | Estimated εΦ | τ/ms | $\lambda_{exc}$/nm |
|---|---|---|---|---|
| 19 | 83000 | 14100 | 0.93 | 323 |
| 46 | 64000 | 16400 | 0.70 | 343 |
| 48 | 69000 | 13800 | 0.77 | 340 |
| 59 | 139000 | 12600 | 0.94 | 320 |
| 75 | 82000 | 16400 | 0.79 | 347 |

Figure 15B:
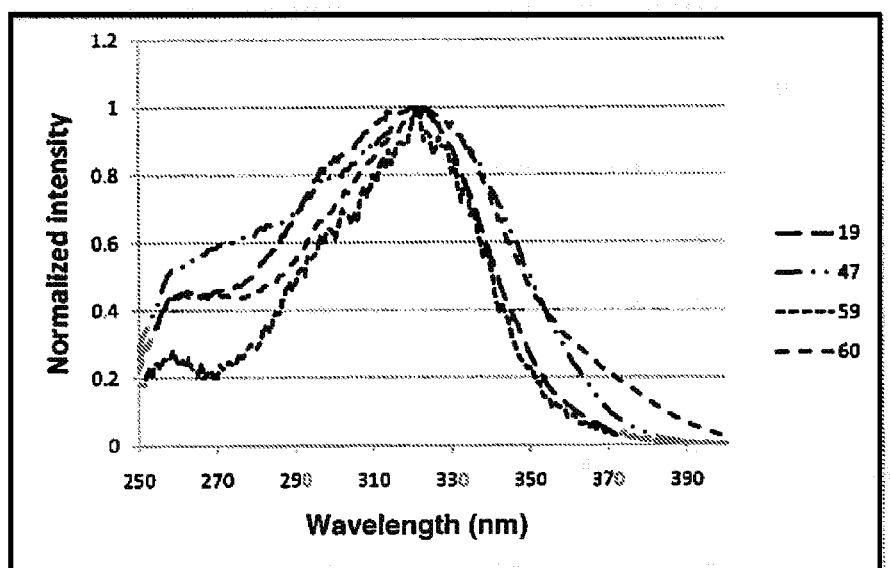
FIG. 15B shows the excitation maxima of chelates 19, 47, 59, and 60.

Excitation maxima of chelates 46, 48 and 75 are presented in FIG. 15A as well as chelates 19, 47, 59 and 60 in FIG. 15B, to show the broad excitation area offering the possibility to use cheap LED based excitation possibilities.

Example 73

Labelling of antibody with chelates 19, 43, 45 and 74

The TnI labeled antibodies were prepared as described in Example 17. The measured photo-physical properties excitation wavelengths ($\lambda_{exc}$), luminescence decay times (τ), molar absorptivities (ε), luminescence yields (εΦ) of the labelled cTnIs with the chelates 19, 43, 45 and 74 in 50 mM TRIS buffer (pH 7.75) in the Table 4.

Dry measurements (19(dry), 43(dry), 45(dry) and 74(dry)) represents estimated luminescence yields based on the signal measurements after dry immunoassay done as described in the Example 18.

TABLE 4

| Compound | ε/M$^{-1}$cm$^{-1}$ | Estimated εΦ | τ/ms | $\lambda_{exc}$/nm |
|---|---|---|---|---|
| 19 | 70000 | 9100 | 0.90 | 323 |
| 19 (dry) | | 10200 | | |
| 43 | 78000 | 11400 | 0.69 | 344 |
| 43 (dry) | | 20700 | | |
| 45 | 88000 | 6800 | 0.66 | 343 |
| 45 (dry) | | 9000 | | |
| 74 | 110000 | 11600 | 0.71 | 350 |
| 74 (dry) | | 13700 | | |

The invention claimed is:
1. A lanthanide chelating ligand of the formula (II),

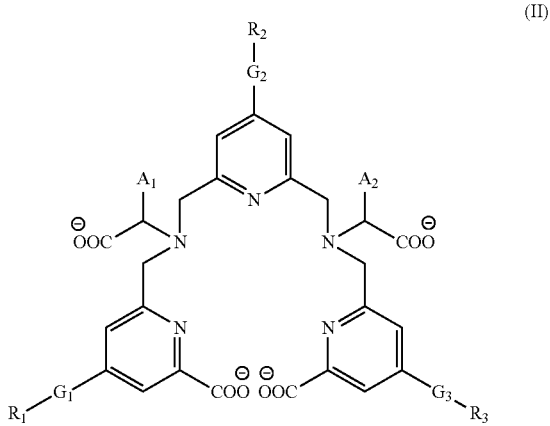

wherein
each of $G_1$, $G_2$ and $G_3$ is independently an optionally substituted phenylethynyl conjugating group,
wherein each of $G_1$ and $G_3$ is unsubstituted or is mono-$R_4$-substituted, di-$R_4$,$R_5$-substituted, or tri-$R_4$,$R_5$,$R_6$-substituted and $G_2$ is unsubstituted or mono-$R_4$-substituted,
wherein $R_4$, $R_5$, and $R_6$ are independently selected from the group consisting of —$OR_9$ and —$SR_9$,
wherein $R_9$ is selected from the group consisting of —$(CH_2)_{1-6}COOH$, —$(CH_2)_{1-6}COO^-$, and a monosaccharide,
wherein each of $R_1$ and $R_3$ is hydrogen;
wherein $R_2$ is a reactive group Z selected from amino (—$NH_2$) or isothiocyanato (—NCS), and
wherein each of $A_1$ and $A_2$ is hydrogen.

2. The lanthanide chelating ligand according to claim 1, wherein the chelating ligand further includes $Na^+$ as a counter ion.

3. The lanthanide chelating ligand of the formula (II) according to claim 1, wherein $R_2$ is a reactive group Z that is isothiocyanato (—NCS).

4. The lanthanide chelating ligand of the formula (II) according to claim 1, wherein $R_9$ is selected from the group consisting of —$(CH_2)COOH$ and —$(CH_2)COO^-$.

5. The lanthanide chelating ligand of the formula (II) according to claim 1, wherein $R_9$ is —$(CH_2)COO^-$.

6. The lanthanide chelating ligand of the formula (II) according to claim 5, wherein $R_2$ is a reactive group Z that is isothiocyanato (—NCS).

7. A solid support material conjugated with the lanthanide chelating ligand of formula (II) according to claim 1.

8. A luminescent lanthanide chelate selected from the group consisting of:

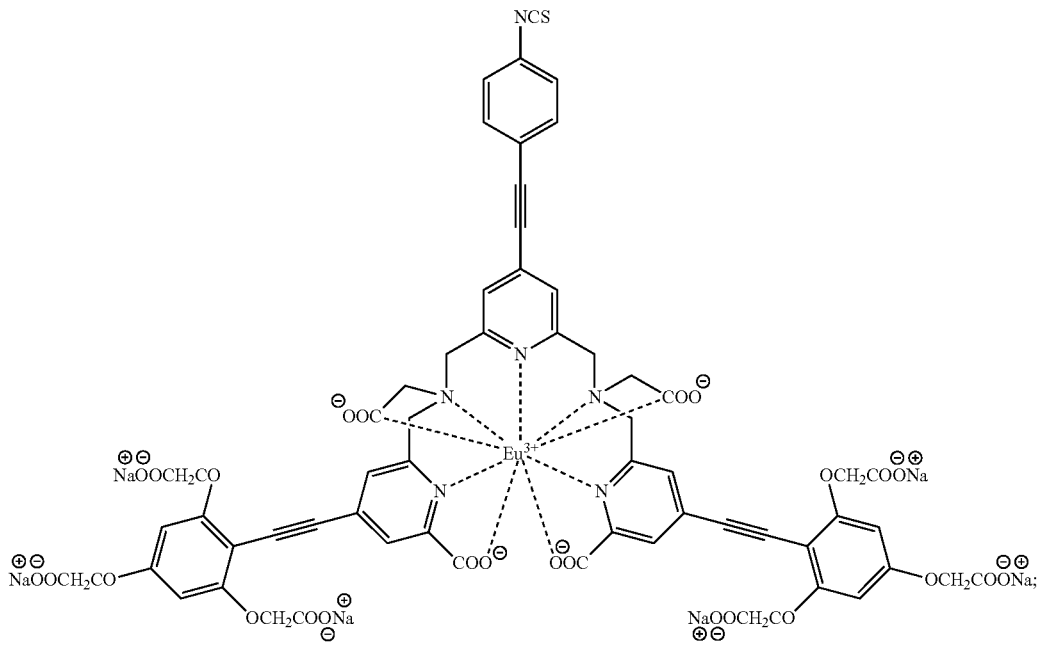

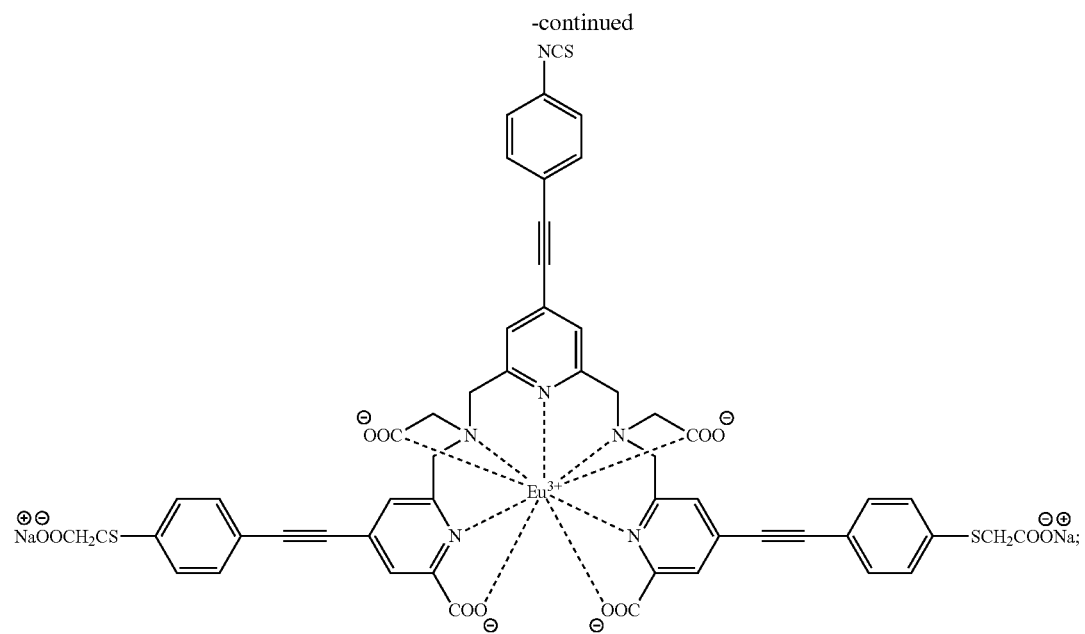
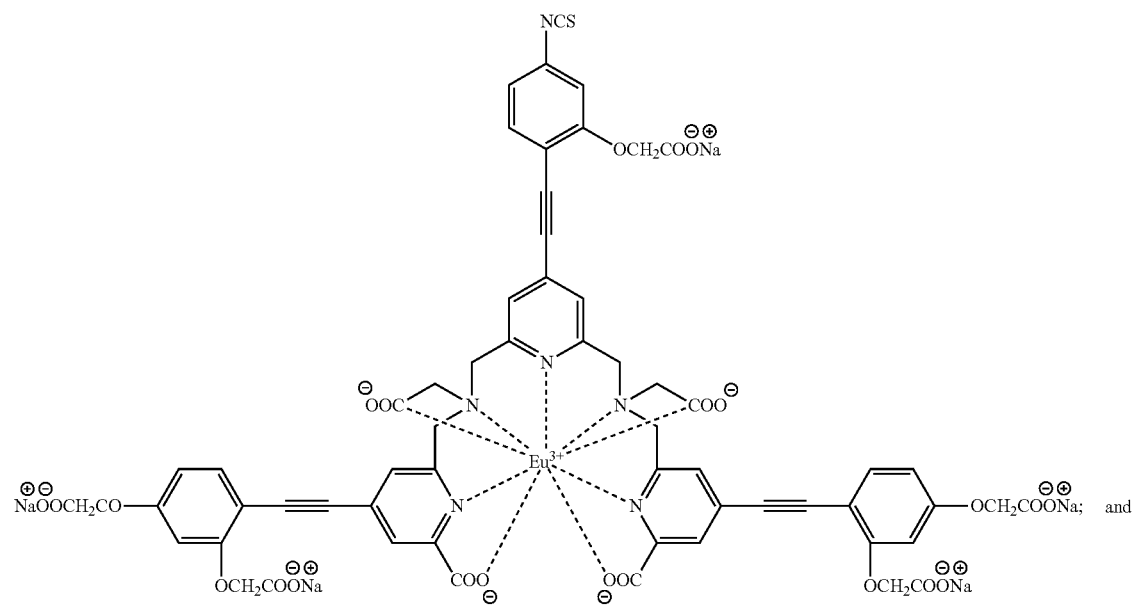

-continued
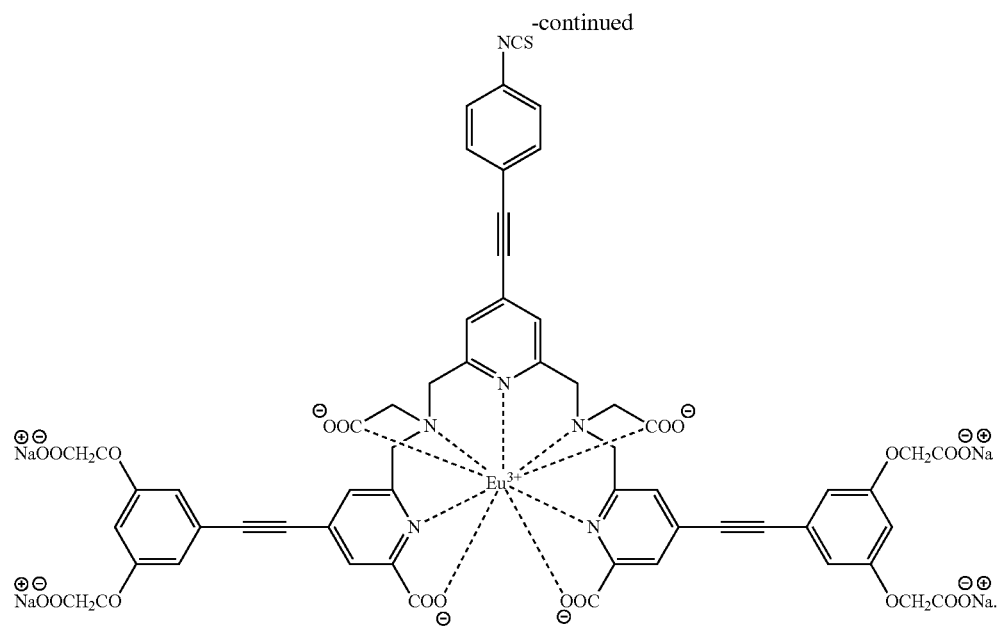
9. The luminescent lanthanide chelate according to claim 8 which is
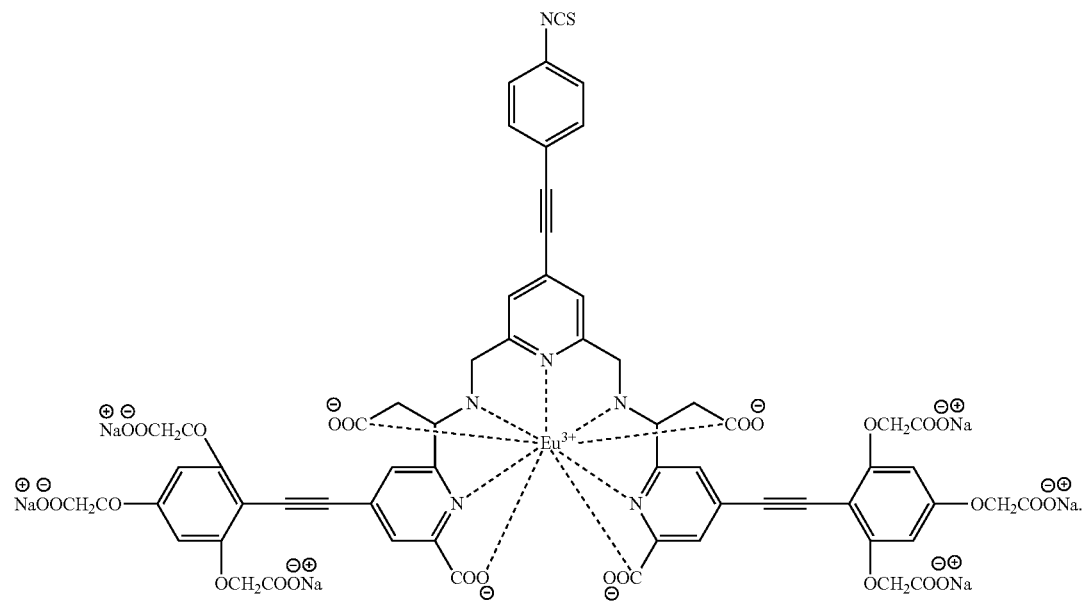
10. The luminescent lanthanide chelate according to claim 8, which is

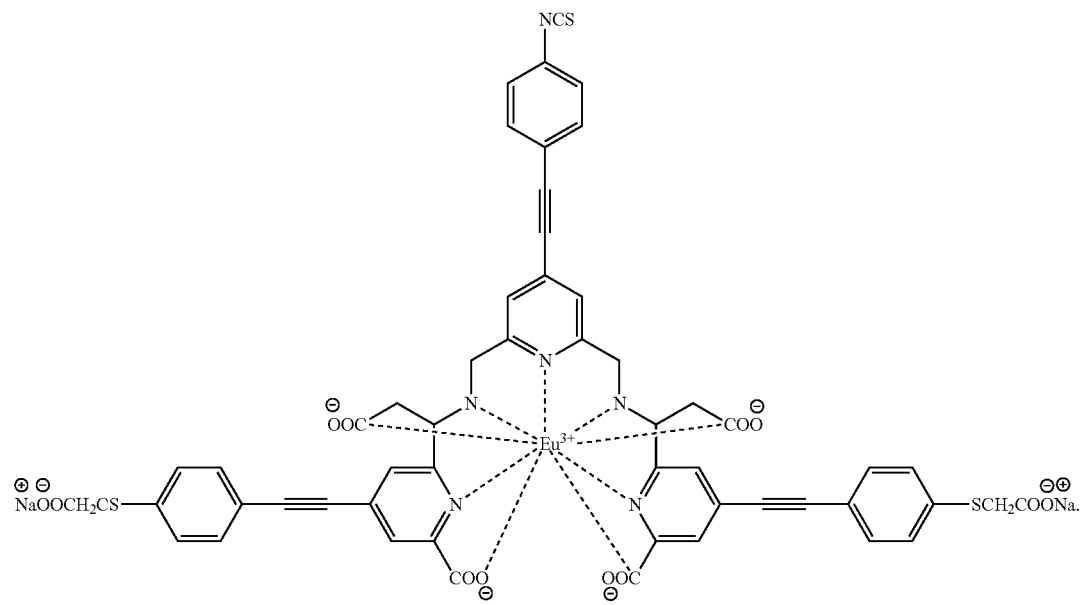
11. The luminescent lanthanide chelate according to claim 8 which is
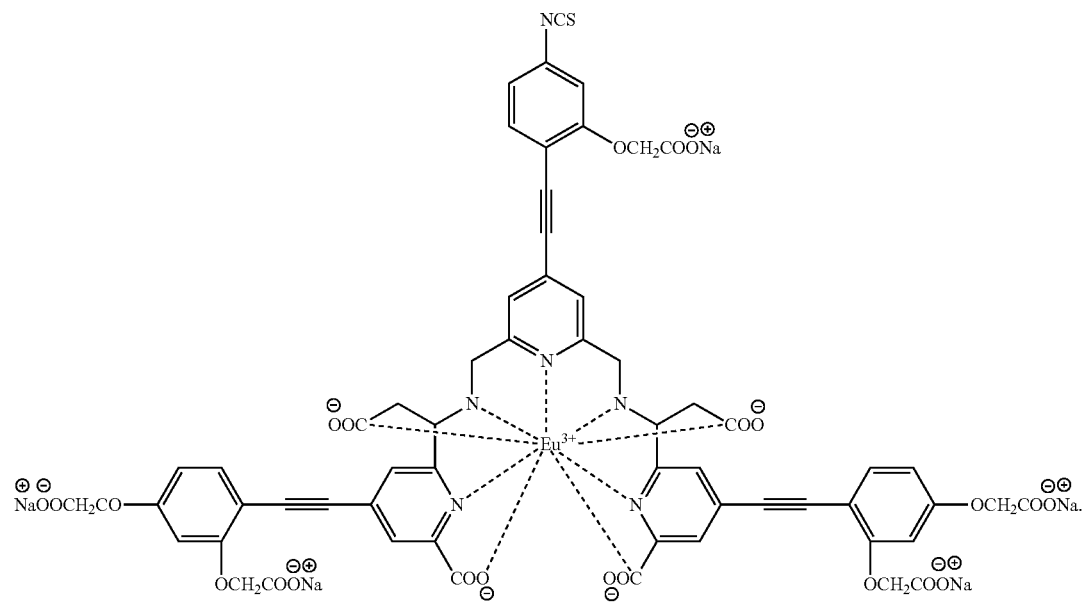
12. The luminescent lanthanide chelate according to claim 8 which is

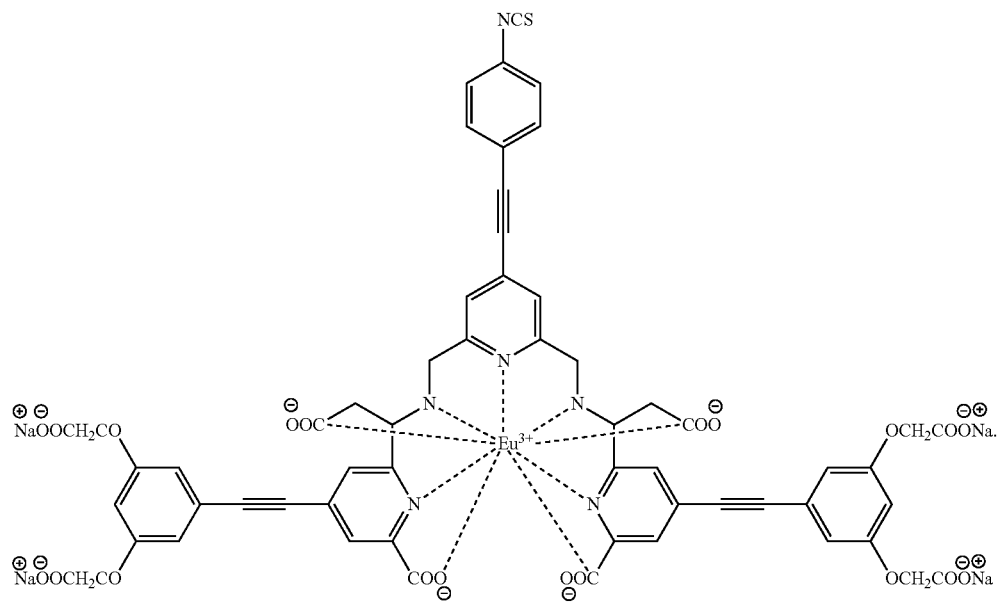

13. A method of carrying out a biospecific binding assay, said method comprising the steps of:

a) forming a biocomplex between an analyte and a biospecific binding reactant labelled by the lanthanide chelate according to claim 8;

b) exciting said biocomplex with radiation having an excitation wavelength, thereby forming an excited biocomplex; and c) detecting emission radiation emitted from said excited biocomplex.

* * * * *